United States Patent
McDuff et al.

(10) Patent No.: US 11,232,290 B2
(45) Date of Patent: Jan. 25, 2022

(54) IMAGE ANALYSIS USING SUB-SECTIONAL COMPONENT EVALUATION TO AUGMENT CLASSIFIER USAGE

(71) Applicant: Affectiva, Inc., Waltham, MA (US)

(72) Inventors: Daniel McDuff, Cambridge, MA (US); Rana el Kaliouby, Milton, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 15/395,750

(22) Filed: Dec. 30, 2016

(65) Prior Publication Data

US 2017/0109571 A1     Apr. 20, 2017

Related U.S. Application Data

(63) Continuation-in-part of application No. 15/262,197, filed on Sep. 12, 2016, now abandoned, which is a
(Continued)

(51) Int. Cl.
*G06K 9/62* (2006.01)
*G06K 9/46* (2006.01)
(Continued)

(52) U.S. Cl.
CPC ........ *G06K 9/00302* (2013.01); *A61B 5/0077* (2013.01); *A61B 5/1176* (2013.01);
(Continued)

(58) Field of Classification Search
CPC ............... A61B 5/04; A61B 5/16; A61B 5/48
See application file for complete search history.

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

"Face recognition using HOG-EBGM" by A. Albiol et al. Pattern Recognition Letters. 29 (2008) 1537-1543.*

(Continued)

*Primary Examiner* — Jason M Ip
(74) *Attorney, Agent, or Firm* — Adams Intellex, PLC

(57) ABSTRACT

Images are analyzed using sub-sectional component evaluation in order to augment classifier usage. An image of an individual is obtained. The face of the individual is identified, and regions within the face are determined. The individual is evaluated to be within a sub-sectional component of a population based on a demographic or based on an activity. An evaluation of content of the face is performed based on the individual being within a sub-sectional component of a population. The sub-sectional component of a population is used for disambiguating among content types for the content of the face. A Bayesian framework that includes a conditional probability is used to perform the evaluation of the content of the face, and the evaluation is further based on a prior event that occurred.

28 Claims, 15 Drawing Sheets

Related U.S. Application Data continuation-in-part of application No. 14/796,419, filed on Jul. 10, 2015, now abandoned, which is a continuation-in-part of application No. 14/460,915, filed on Aug. 15, 2014, now abandoned, said application No. 14/796,419 is a continuation-in-part of application No. 13/153,745, filed on Jun. 6, 2011, now abandoned, said application No. 14/460,915 is a continuation-in-part of application No. 13/153,745, filed on Jun. 6, 2011, now abandoned.

(60) Provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | |
|---|---|
| *A61B 5/16* | (2006.01) |
| *G06Q 30/02* | (2012.01) |
| *A61B 5/00* | (2006.01) |
| *G06K 9/32* | (2006.01) |
| *G16H 50/70* | (2018.01) |
| *A61B 5/1171* | (2016.01) |
| *G16H 30/40* | (2018.01) |
| *G16H 50/30* | (2018.01) |
| *G16H 20/70* | (2018.01) |
| *G06K 9/00* | (2006.01) |
| *G16H 40/67* | (2018.01) |

(52) U.S. Cl.
CPC ............ *A61B 5/165* (2013.01); *A61B 5/7264* (2013.01); *G06K 9/0053* (2013.01); *G06K 9/00335* (2013.01); *G06K 9/3241* (2013.01); *G06K 9/4642* (2013.01); *G06K 9/6218* (2013.01); *G06K 9/6278* (2013.01); *G16H 20/70* (2018.01); *G16H 30/40* (2018.01); *G16H 50/30* (2018.01); *G16H 50/70* (2018.01); *A61B 5/6898* (2013.01); *G06Q 30/0242* (2013.01); *G06T 2207/10016* (2013.01); *G06T 2207/30201* (2013.01); *G16H 40/67* (2018.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 * | 2/2006 | Hsieh ................ G06T 7/246 382/103 |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |

(56) References Cited

U.S. PATENT DOCUMENTS

| | | | |
|---|---|---|---|
| 7,307,636 B2 | 12/2007 | Matraszek et al. | |
| 7,319,779 B1* | 1/2008 | Mummareddy | G06K 9/00288 |
| | | | 382/118 |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,747,801 B2 | 6/2010 | Han et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1* | 4/2011 | Sharma | G06Q 20/3674 |
| | | | 705/14.49 |
| 3,010,458 A1 | 8/2011 | Galbreath et al. | |
| 8,022,831 B1 | 9/2011 | Wood-Eyre | |
| 8,219,438 B1 | 7/2012 | Moon et al. | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1 | 5/2003 | Dimitrova et al. | |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2005/0187437 A1* | 8/2005 | Matsugu | A61B 5/16 |
| | | | 600/301 |
| 2005/0283055 A1 | 12/2005 | Shirai et al. | |
| 2005/0289582 A1 | 12/2005 | Tavares et al. | |
| 2006/0019224 A1 | 1/2006 | Behar et al. | |
| 2006/0143647 A1 | 6/2006 | Bill | |
| 2006/0235753 A1 | 10/2006 | Kameyama | |
| 2007/0167689 A1 | 7/2007 | Ramadas et al. | |
| 2007/0173733 A1 | 7/2007 | Le et al. | |
| 2007/0239787 A1 | 10/2007 | Cunningham et al. | |
| 2007/0255831 A1 | 11/2007 | Hayashi et al. | |
| 2007/0265507 A1 | 11/2007 | de Lemos | |
| 2007/0299964 A1 | 12/2007 | Wong et al. | |
| 2008/0059570 A1 | 3/2008 | Bill | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0287821 A1 | 11/2008 | Jung et al. | |
| 2008/0292151 A1 | 11/2008 | Kurtz et al. | |
| 2009/0002178 A1 | 1/2009 | Guday et al. | |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0150919 A1 | 6/2009 | Lee et al. | |
| 2009/0164132 A1 | 6/2009 | Jung et al. | |
| 2009/0210290 A1 | 8/2009 | Elliott et al. | |
| 2009/0217315 A1 | 8/2009 | Malik et al. | |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0299840 A1 | 12/2009 | Smith | |
| 2010/0070523 A1 | 3/2010 | Delgo et al. | |
| 2010/0099955 A1 | 4/2010 | Thomas et al. | |
| 2010/0266213 A1 | 10/2010 | Hill | |
| 2010/0274847 A1 | 10/2010 | Anderson et al. | |
| 2010/0324437 A1 | 12/2010 | Freeman | |
| 2011/0007174 A1* | 1/2011 | Bacivarov | G06K 9/00281 |
| | | | 348/222.1 |
| 2011/0126226 A1 | 5/2011 | Makhlouf | |
| 2011/0134026 A1 | 6/2011 | Kang et al. | |
| 2011/0143728 A1 | 6/2011 | Holopainen et al. | |
| 2011/0144971 A1 | 6/2011 | Danielson | |
| 2011/0196855 A1 | 8/2011 | Wable et al. | |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2012/0324491 A1 | 12/2012 | Bathiche et al. | |
| 2013/0023337 A1 | 1/2013 | Bowers et al. | |
| 2013/0116587 A1 | 5/2013 | Sornmo et al. | |
| 2013/0197409 A1 | 8/2013 | Baxter et al. | |
| 2014/0172910 A1 | 6/2014 | Jung et al. | |
| 2016/0104486 A1 | 4/2016 | Penilla et al. | |
| 2017/0003784 A1 | 1/2017 | Garg et al. | |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

(56) References Cited

OTHER PUBLICATIONS

Albiol, Alberto, et al. "Face recognition using HOG-EBGM." Pattern Recognition Letters 29.10 (2008): 1537-1543.

* cited by examiner

IMAGE ANALYSIS USING SUB-SECTIONAL COMPONENT EVALUATION TO AUGMENT CLASSIFIER USAGE

RELATED APPLICATIONS

This application claims the benefit of U.S. provisional patent application "Image Analysis Using Sub-Sectional Component Evaluation to Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016. This application is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014. The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

FIELD OF ART

This application relates generally to image analysis and more particularly to image analysis using sub-sectional component evaluation to augment classifier usage.

BACKGROUND

Human beings are emotional creatures and exhibit reactions to a variety of external events and internal feelings. Humans can express emotion in a variety of ways, such as by using voice tone and volume, or by gestures of hands and arms, and posture or body stance. However, one of the primary conveyors of emotion is that of facial expressions.

The human face is capable of expressing vast amounts of information and is key for many levels of human communication. Based on both conscious and unconscious positioning and movement of various facial muscles, the human face can form a plethora of facial expressions. The facial expressions can convey moods, emotions and the like. These expressions can include an open, welcoming countenance, a hostile, threatening countenance, and so on. The movements and positions of the facial muscles form expressions that convey emotions, where the emotions range from happy to sad and include angry, fearful, disgusted, and surprised, among many others. The facial expressions of a given person can be captured and analyzed. The facial expression analysis can be undertaken for purposes including facial recognition and facial identification, among other applications, and can determine a range of emotions and mental states. The mental states can include frustration, ennui, confusion, cognitive overload, skepticism, delight, satisfaction, calmness, stress, and many others.

Various human expressions can be recognized. For example, a smile is one of the most recognized emotions throughout the world. When smiling or laughing, the cheeks are pulled up and out, and the mouth sides are pulled backwards as well as slightly upwards. This slight upper movement pushes the upper eyelids and produces wrinkles around the eyes. Additionally, the mouth appears to get closer to the nose. A smile may indicate happiness. However, a smile can indicate other emotions as well. For example, an asymmetrical smile, formed by raising one side of the lips, can be indicative of contempt. There are many other mental states and facial expressions that are within the range of human emotion.

Gaining insight into the mental states of individuals represents an important tool for understanding events. For example, in advertising, understanding the resultant mental states of viewers of the advertisements is valuable for gauging the efficacy of those advertisements. However, it is very difficult to properly interpret mental states when the individuals under consideration may themselves be unable to accurately communicate their mental states. Furthermore, different people may respond differently to a given stimulus. For example, some people may smile when afraid or nervous. Thus, there is a difference between a facial expression and a mental state. The smile a person produces when nervous may be different than the smile produced when the person is happy.

Mental or emotional state can play a role in how people interpret external stimuli. Emotions such as happiness, sadness, fear, laughter, relief, angst, worry, anguish, anger, regret, and frustration are often reflected in facial expressions. Thus, the study of facial expressions and their meanings can provide important insight into human behavior.

SUMMARY

One or more images of an individual are obtained. The one or more images can be obtained using a variety of image capture devices including cameras. A face of the individual is identified within the one or more images. In embodiments, facial landmarks of the face of the individual are determined. The individual is evaluated to be within a sub-sectional component of a population. In embodiments, the performing the evaluation of content of the face is further based on a prior probability that occurred. This can be based on a sub-sectional component. For example, the evaluation of content can include evaluation of the probability that a facial expression is a smile given that the individual undergoing the facial expression analysis belongs to a particular demographic and/or experiential sub-sectional component. A different threshold can be used for determining an emotion based on the sub-sectional component of the individual. The threshold adjustment can be based on a demographic sub-sectional component, such as ethnicity and/or gender. The threshold adjustment can be based on an experiential sub-sectional component, such as if the user is watching content at a movie theater or on a tablet computer. In embodiments, the content of the face includes emotional content, and the emotional content comprises a facial expression. In embodiments, the performing the evaluation of content of the face includes evaluation of action units for the content of the face. Furthermore, in embodiments, the sub-sectional component of a population includes age, ethnicity, culture or gender. An evaluation of content of the face is performed based on evaluating of the individual to be within a sub-sectional component of a population. Thresholds and/or sensitivity settings can be adjusted based on an identified sub-sectional component for an individual undergoing an expression analysis. Thus, in embodiments, performing the evaluation of content of the face is based on modulating a sensitivity to an emotional content. The sub-sectional component of a population is used for disambiguating among a plurality of content types for the content of the face. In embodiments, the sub-sectional component is determined based on an activity in which the individual is participating. The activity can include, but is not limited to, watching television, using an e-reader, reading a magazine, playing a video game, listening to music, and so on. In embodiments, the sub-sectional component is determined based on information pertaining to prior experiential information for the individual. In embodiments, the administrative application has access to prior experiential information such as a viewing history. The viewing history can include a list of previously watched videos. In some embodiments, compensation of the expression intensity is performed based on the prior experiential information. For example, when an individual laughs based on some humorous content that has previously been viewed, the intensity of the laugh might be lower than when the video was viewed for the first time, since the individual might know what is going to happen in the video. Thus, the expression can be compensated since the individual previously viewed the video. For example, a "medium" laugh from a previously watched video can be equivalent to a "large" laugh from a video being viewed for the first time.

In embodiments, the evaluation of the content of the face is based on image classifiers, and the performing the evaluation of the content of the face is based on modifying emotion classifiers. In embodiments, the performing the evaluation of the content of the face is based on a Bayesian framework, and the Bayesian framework includes a conditional probability based on the individual being within the sub-sectional component of the population.

A computer-implemented method for image analysis is disclosed comprising: obtaining an image of an individual; identifying a face of the individual; evaluating the individual to be within a sub-sectional component of a population; and performing, using one or more processors, an evaluation of content of the face based on the evaluating of the individual to be within the sub-sectional component of the population. In embodiments, a computer program product embodied in a non-transitory computer readable medium for image analysis is provided, where the computer program product comprises: code which causes one or more processors to perform operations of: obtaining an image of an individual; identifying a face of the individual; evaluating the individual to be within a sub-sectional component of a population; and performing an evaluation of content of the face based on the evaluating of the individual to be within the sub-sectional component of the population. In some embodiments, a computer system for image analysis comprises: a memory which stores instructions; one or more processors attached to the memory wherein the one or more processors, when executing the instructions which are stored, are configured to: obtain an image of an individual; identify a face of the individual; evaluate the individual to be within a sub-sectional component of a population; and perform an evaluation of content of the face based on the evaluating of the individual to be within the sub-sectional component of the population.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
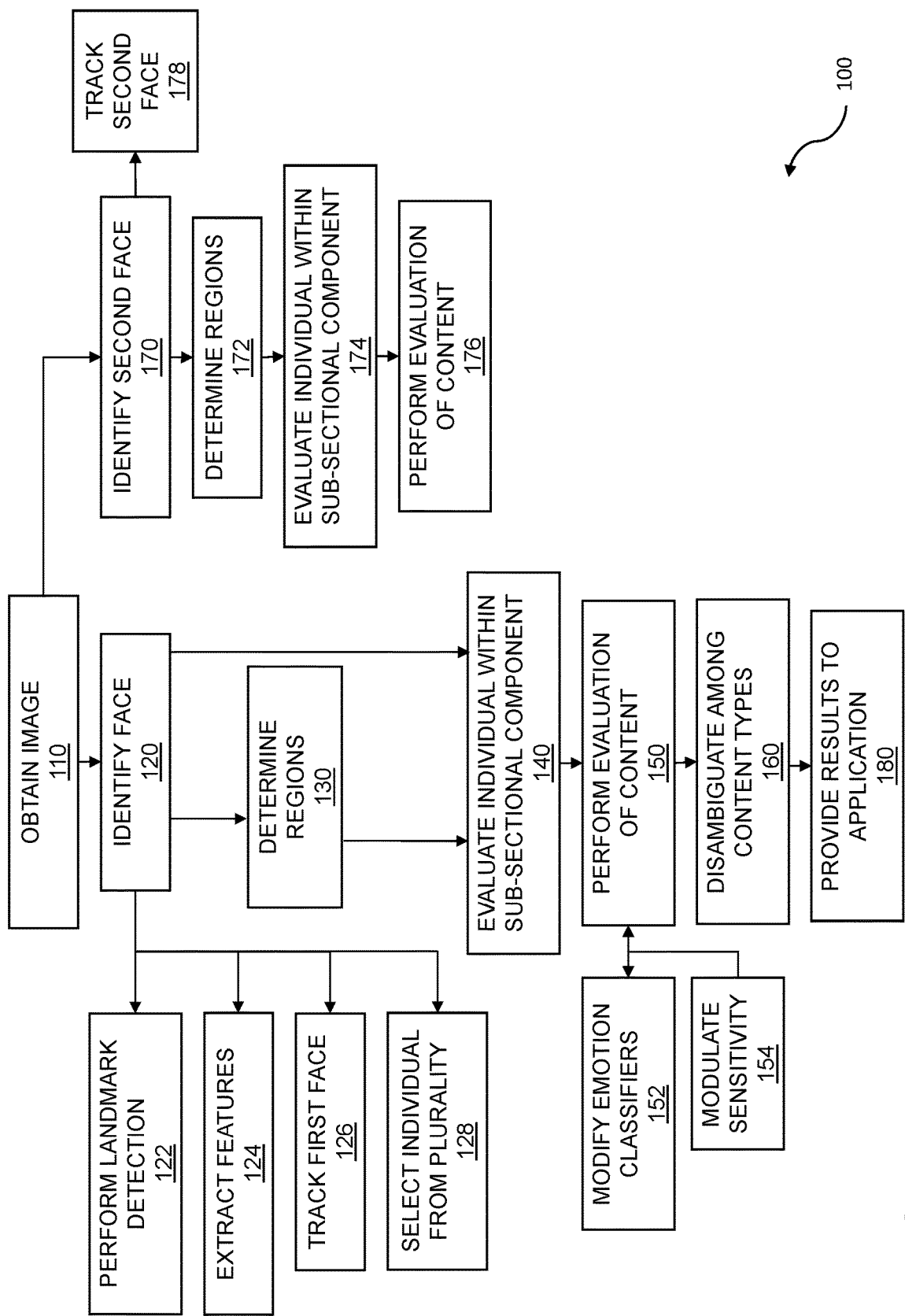
FIG. 1 is a flow diagram for analysis using sub-sectional components.

Humans observe and process stimuli from the environments around them by experiencing their surroundings using their senses. Sensing can include experiencing objects, animals, or other humans using sight, hearing, smell, touch, and so on. Typically, the experiencing of other humans includes interacting with those people. Human interaction, including communication, is in large part based on observing each other's faces. Regardless of whether the interactions include sound, smell, touch, or any of the other senses, sight plays a fundamental role in social interaction. Being able to observe the face of another person is critical because the human face is highly expressive. The various facial expressions that are exhibited range widely and can convey a mental state of a person, an emotional state of a person, and so on. For example, a sultry smile communicates a very different message to the recipient of the smile than does an angry frown. In another example, a neutral expression can indicate, boredom, inattention, indifference, and so on. Effective communication of information is the basis of a social exchange between or among other people and greatly influences how the interaction progresses. A flirtatious smile might attract people to the interaction and retain them in it, while an angry frown can cause people to leave the interaction, perhaps expediently.

Facial expressions can communicate different information among various people depending to which sub-sectional component of a population they belong. A smile or a frown, for example, can communicate different information among different groups of people. The differences in the information that is communicated can depend on many factors, such as demographics including age, ethnicity, culture, gender, and so on. The facial expressions can vary depending on a particular situation or context. In some cases, both a closed-lip smile and a chuckle while reading an amusing passage in an e-book and an opened-lip smile and loud laugh while watching a humorous scene in a movie or television program can both indicate amusement, happiness, engagement, and so on, but the outward manifestations of these similar reactions can be quite different. In another example, the telling of a joke can result in great mirth for one sub-sectional component of a population, while the same joke told to another sub-sectional component of a population can result in offense instead of amusement.

In this technique, one or more images of an individual are obtained. The images can be captured using a camera or another image capture device; a sensor; etc. The images can be videos, frames of a video, still images, or other image capture media. The face of the individual is identified in an image. In some embodiments, regions within the face of the individual are determined, where the regions can include eyebrows, eyes, a nose, a mouth, ears, etc. The individual is evaluated to be within a sub-sectional component of a population. The sub-sectional component of the population can include a demographic, and the demographic can include age, ethnicity, culture, or gender. Conversely, the sub-sectional component of the population can be based on an activity performed by a person or group of people. In essence, mental state analysis is performed in light of the context in which facial data is collected. The context provides information about the person or about what the person is doing. An evaluation of content of the face is performed based on an evaluation of the individual to be within a sub-sectional component of a population.

FIG. 1 is a flow diagram for analysis using sub-sectional components. The flow 100, or portions thereof, can be implemented using a mobile device, a server, a semiconductor chip, a cloud processor, and so on. The flow 100 describes image analysis using sub-sectional component evaluation to augment classifier usage. The flow 100 includes obtaining an image 110 of an individual. The image of the individual can be captured with a camera, where the camera can be any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image can be a still image, a frame from a video, a video, and so on. The image can be one image from a series of images of the individual. The series of images can include a video of the individual.

The flow 100 includes identifying a face 120 of the individual. A given image that is obtained can include objects, animals, people, etc. When a person is found in the image, the image can be analyzed to locate the face of the person in the image. The face can be identified in the image using a variety of image processing and analysis techniques including edge detection, gradient calculation, and so on. A bounding box can be placed around the face to indicate the location of the face. The flow 100 includes performing facial landmark detection 122 on the face of the individual. The facial landmark detection can include detecting the edges of eyebrows, the corners of a mouth, the tip of a nose, the edges of eyes, etc. The flow 100 includes extracting features 124 within the face of the individual. The features that can be extracted within the face can include eyebrows, eyes, a nose, a mouth, and so on. The flow 100 includes tracking the face 126 within the video. The tracking the face can include rotation and translation of the face within the video, the face leaving the video, the face returning to the video, and so on. The flow 100 includes selecting the individual from a plurality 128 of people. A particular face can be selected in a video when two or more faces are present in the video.

The flow 100 can also include determining regions 130 within the face of the individual. The regions of the face can include one or more of eyebrows, eyes, nose, mouth, ears, etc. In embodiments, the determining includes facial landmarks. The flow 100 includes evaluating the individual to be within a sub-sectional component 140 of a population. The sub-sectional component can be determined based on a demographic. Any appropriate demographic can be considered in the determining. The sub-sectional component can be determined based on an activity in which the individual is participating. The sub-sectional component can be determined based on information pertaining to prior experiential information for the individual. The sub-sectional component can be based on a demographic and the demographic can include an age, ethnicity, culture, or gender. In embodiments, image classifiers are used to map facial landmarks within the face to emotional content. The emotional content can include a facial expression. The facial expression can include, but is not limited to, a frown, a smile, a laugh, a grimace, an expression of fear, pain, sadness, joy, attentiveness, empathy, anger, and frustration, among others. The emotional content that can be detected in the face can include detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In embodiments, the evaluation of content of the face is based on a mental state event temporal signature. The temporal signature for content of the face can include an event, an external stimulus, etc. For example, a smile can be detected as correlating with an amusing event occurring in a media presentation, or as a result of a person telling a funny joke.

The flow 100 includes performing an evaluation of content 150 of the face based on the evaluating of the individual to be within a sub-sectional component of a population. The content of the face can include facial expressions, emotions, moods, mental states, and so on. More than one content type can be evaluated for a face. The content type can include a smile. The facial content can include emotional content. The performing the evaluation of the content of the face can be based on a Bayesian framework. The Bayesian framework can include a conditional probability based on the individual being within a sub-sectional component of the population. The performing the evaluation of content of the face can be further based on a prior probability that occurred: in other words, given the prior probability that earlier facial content was present, the probability that the current facial content is one type is more likely than the probability of another type. The evaluation of content of the face can be based on motion of the regions. For example, the eyebrows can rise, the eyes can close, the mouth can open into a smile, etc.

In some embodiments, evaluating an individual to be within the sub-sectional component is based on applying image classifiers to the face. In embodiments, the evaluation of the content of the face is based on modifying emotion classifiers. Classifiers can be modified through structured or unstructured learning. In embodiments, the modifying is based on the individual being within the sub-sectional component of the population. In a supervised learning scenario, a plurality of training images can be input to a system that uses image classifiers. The training images can be human-tagged with various attributes such as gender, ethnicity, and/or age range of the individual(s) in the image. The human-tagged images can serve as training images to fine-tune weights and adjustments within the image classifiers. In embodiments, the human-tagged images are self-tagged images. That is, an individual can submit an image of themselves and indicate what the sub-sectional components (demographic and/or experiential) are to be associated with that image.

In embodiments, the image classifiers are learned using deep learning techniques. Deep learning is a type of machine learning utilizing neural networks. In general, it is non-trivial for a computer to interpret the meaning of raw sensory input data, such as digital images that are represented as an array of pixels. Converting from an array or subset of pixels to identification of an object within the image, such as a human face, is a very complicated effort. Direct evaluation of this mapping is computationally impractical to solve directly. However, embodiments disclosed herein comprise a multilayered analysis engine that utilizes deep learning. The multilayered analysis engine can determine features within an image by dividing the highly complex mapping into a series of more simple mappings, each processed by a different layer of the multilayered analysis engine. The input image is presented to an input layer, which performs initial processing on the image. Then, one or more hidden layers extract features from the image. In embodiments, the outputs of the hidden layers are not directly observable. The hidden layers can provide evaluation of mental states or facial expressions without specific interpretation or labels being provided. The outputs of the hidden layers can, however, be used by further layers within a convolutional neural network to perform the mental state or facial expression analysis.

Convolutional neural networks (CNNs) share many properties with ordinary neural networks. For example, they both include neurons that have learnable weights and biases. Each node/neuron receives some inputs and performs a function that determines if the node/neuron "fires" and generates an output. However, CNNs are well-suited for inputs that are images, allowing for certain optimizations to be incorporated into the architecture of the CNN. These then make the forward function more efficient to implement and improve the performance regarding image analysis.

When an image is input to the multilayered analysis engine, the input layer can be used to identify edges by comparing the brightness of neighboring pixels or other edge detection process. The edges can then be input to a subsequent hidden layer, which can then extract features such as corners. The process continues with additional hidden layers, each additional layer performing additional operations, and culminating with an output layer that produces a result which includes a facial expression and/or mental state. Thus, the deep learning network provides an improved automated detection of facial expressions and/or mental states, enabling new and exciting applications such as large-scale evaluation of emotional response.

The performing the evaluation of content of the face can be based on modulating a sensitivity 154 to an emotional content. In some cases, one sub-sectional component of a population can be less likely to have certain facial content than another sub-sectional component of the population. For this example, sensitivity to an emotion content can be modulated (e.g. adjust gain) in order to better detect the emotion content. The performing the evaluation of the content of the face can be based on image classifiers. The performing the evaluation of the content of the face can be based on emotion classifiers. The classifiers can be an algorithm, a heuristic, a segment of code, and so on. The performing the evaluation of the content of the face can be based on modifying emotion classifiers 152. The modifying can be based on the individual being within a sub-sectional component of the population. The modifying can be based on age, ethnicity, culture, gender, level of education, income level, and so on. A major shortcoming of current technology in this area is that it does not account for variations by sub-sectional component. Cultural and environmental differences can widely affect the range of expressed human emotion, making automated analysis challenging. Thus, disclosed embodiments provide a significant improvement in the capability of computerized facial expression recognition by factoring in one or more sub-sectional components into the evaluation and generated result.

The flow 100 includes disambiguating among a plurality of content types 160 for the content of the face based on the sub-sectional component of a population. In some cases, a content type can include a smile. A smile can be formed by raising the corners of the mouth and can include lips together, lips apart, etc. The characteristics of a smile can depend on the sub-sectional component of a population. For example, a smile expressed by one ethnic group can be different from a smile to another ethnic group, and so on. The disambiguating of the facial content can be further based on experiential context for the individual. The experiential context can be based on a current experience, a prior experience, an experience baseline, and so on.

The flow 100 continues with providing results to an application 180. The results can include numbers and/or percentages of people that experienced a particular emotion. The results can further include an intensity level histogram that indicates the range of emotion and the distribution of samples within that range. The results can further include a listing of numbers and/or percentages categorized by sub-sectional components. As an example, a marketing research firm, wishing to gauge response to a funny commercial, can present the commercial to people belonging to various sub-sectional components. The sub-sectional components can be demographic and/or experiential. The marketing research firm then receives, via an application, results based on mental state analysis of people in multiple sub-sectional components. As an example, they might receive information that 45 percent of females reacted to the commercial with a smile, while 67 percent of males reacted to the commercial with a smile. The sub-sectional components can include categories ascertained from questionnaires. These sub-sectional components can include, but are not limited to, level of education, occupation, income bracket, age, and the like. Thus, continuing with the example, the marketing firm might receive information that 41 percent of college-educated people reacted to the commercial with a smile while 74 percent of people without a college education reacted to the commercial with a smile. This type of information can be invaluable to a marketing firm or another entity that needs to gauge the effectiveness of a product such as a commercial, video, television show, and/or movie. Embodiments include providing results of the performing the evaluation of the content of the face to an administrative application. Thus, an application can retrieve the mental state data from a plurality of individuals organized by sub-sectional component.

In embodiments, the administrative application uses a software developer kit (SDK) interface. This allows various third-party vendors or users to develop a custom application based on the SDK. The SDK can provide various application programmers interface (API) functions to allow developers to make applications that retrieve mental state data based on sub-sectional components. The SDK can provide callback functions to handle image capture and processing results of individual frames of video. The SDK can provide a function to return an appearance data structure based on a detected face. The appearance data structure can include a gender value. In embodiments, the gender value is male, female, neutral, and/or unknown. The appearance data structure can include an age range. In embodiments, the age range includes, but is not limited to, unknown, under 18, 18 to 24, 25 to 34, 35 to 44, 45 to 54, 55 to 64, and/or 65 and over. The appearance data structure can include an ethnicity value. In embodiments, the ethnicity includes, but is not limited to, Caucasian, black/African, south Asian, East Asian, and/or Hispanic. The SDK can provide a function to return an emotion data structure based on a detected face. The emotion data structure can include an array comprising an emotion type enumeration and a corresponding score. In embodiments, the emotion data structure includes, but is not limited to, entries for emotions such as joy, fear, disgust, sadness, anger, surprise, contempt, valence, and/or engagement. In embodiments, the corresponding score for each emotion ranges from zero to 100, with zero being a complete absence of the emotion, and 100 being a maximum amount of expression of the particular emotion. Many more emotions can be analyzed. In embodiments, the evaluation of content of the face includes detection of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The flow 100 includes identifying a second face 170 within the image. In practice, any number of faces in an image can be identified. Thus, in embodiments, the identifying further comprises identifying a second face within the image. In embodiments, the face and the second face are from a plurality of people within the image. For example, in a group photograph, a single face or multiple faces can be analyzed based on an identified sub-sectional component. Thus, embodiments include selecting the individual from a plurality of people.

Embodiments further include an auto-diversification analysis function for group images. In such embodiments, an image including a group of people is analyzed for sub-sectional component categorization. Thus, multiple faces within the group image can be analyzed for demographics such as gender, age range, and/or ethnicity. A sampling of facial expressions from the image can be analyzed, where the sampling of facial expressions is retrieved from a subset of different people within the image. The subset can be selected based on diversity of gender, ethnicity, and/or age. As an example, an image including twenty faces can be analyzed to determine a subset of six faces to use for performing a mental state analysis. The subset can be automatically selected based on diversity. As an example, the subset of six faces can include three male faces, three female faces and can also attempt to include a Caucasian face, an Asian face, an African face, a Hispanic face, and so on, based on the available faces within the image. In this way, a diverse reaction to an event can be automatically analyzed.

The sub-sectional component can include gender, ethnicity, and/or age, among others. Embodiments include identifying a second face within the image; evaluating a person associated with the second face to be within a second sub-sectional component of the population; and performing an evaluation of content of the second face based on the evaluating of the person to be within a second sub-sectional component of the population. In embodiments, the sub-sectional component and the second sub-sectional component are identical.

The flow 100 includes determining regions 172 within the second face. The region within the second face can include one or more of eyebrows, eyes, nose, mouth, and so on. The flow 100 includes evaluating a person associated with the second face to be within a sub-sectional component 174 of a population. The sub-sectional component can be determined based on a demographic. Any appropriate demographic can be considered in the determining. The sub-sectional component can be determined based on an activity in which the individual is participating. The sub-sectional component can be determined based on information pertaining to prior experiential information for the individual. The sub-sectional component can be based on a demographic and the demographic can include an age, ethnicity, culture, or gender. The flow 100 includes performing an evaluation of content 176 of the second face based on the evaluating of the person to be within a sub-sectional component of a population. As was the case for the first face, the content of the second face can include facial expressions, emotions, moods, mental states, and so on. More than one content type can be evaluated for a second face. The facial content can include emotional content. The performing the evaluation of the content of the second face can be based on a Bayesian framework. The Bayesian framework can include a conditional probability based on the individual being within a sub-sectional component of the population. The performing the evaluation of content of the second face can be further based on a prior probability that occurred. The flow 100 includes tracking a second face 178 within the video. The tracking the second face can include rotation and translation of the second face within the video, the second face leaving the video, the second face returning to the video, and so on. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on.

Figure 2:
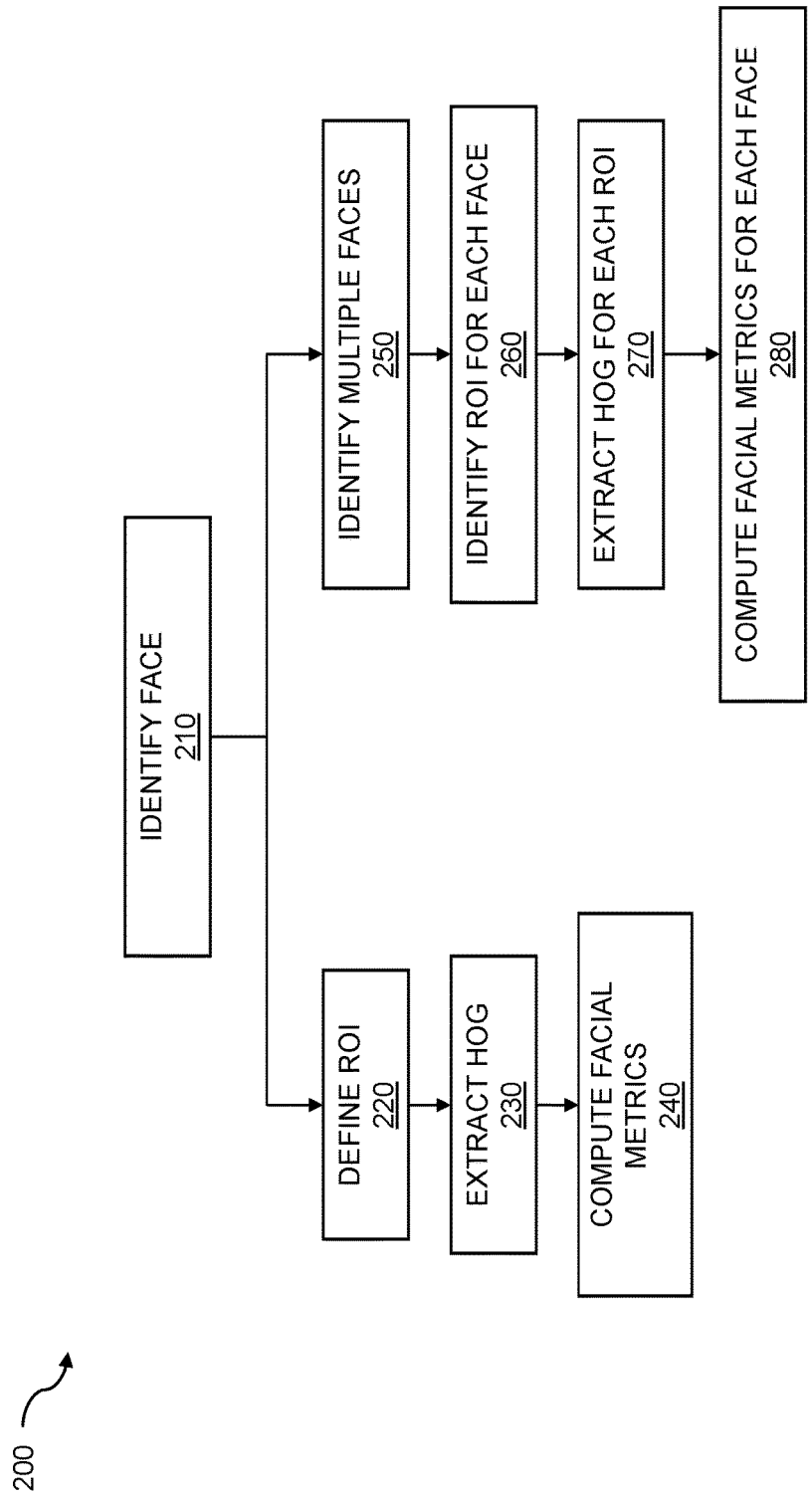
FIG. 2 is a flow diagram for computing facial metrics.

FIG. 2 is a flow diagram for computing facial metrics. The flow 200 can be implemented on a mobile device, on a server, in a semiconductor chip, and so on. Sub-sectional components can be used with performing the evaluation of content of the face, including computing facial metrics. The sub-sectional components can be used to provide a context. The flow 200 describes computing facial metrics for one or more faces identified in images. The flow 200 includes identifying a face 210 of the individual in an image of an individual. Various techniques can be used to identify the face of the individual in the image, including image analysis techniques. The flow 200 includes defining a region of interest (ROI) 220 in the image that includes the face. The region of interest can be located in a face based on facial landmark points such as edges of nostrils, edges of a mouth, edges of eyes, etc. The flow 200 includes extracting one or more histogram-of-oriented-gradients (HoG) 230 features from the ROI. A HoG can be based on a count of occurrences of gradient orientation, where the gradient orientation can be within a given section of an image. The gradients can be based on intensity. The flow 200 includes computing a set of facial metrics 240 based on the one or more HoG features. The facial metrics can be used to identify the locations of facial features such as a nose, a mouth, eyes, ears, and so on. The flow 200 includes identifying multiple human faces 250 within the image. The captured image that can be analyzed for the presence of one person can be analyzed for the presence of two or more people. The flow 200 includes defining a region of interest (ROI) in the image for each identified human face 260. The regions of interest for the one or more faces can include facial landmarks. The flow 200 includes extracting one or more HoG features from each ROI 270. The HoG can include facial feature descriptors and can be computed for the regions of interest. The flow 200 includes computing a set of facial metrics based on the one or more HoG features for each of the multiple human faces 280. As mentioned above, the facial metrics can be used to identify the locations of facial features including facial landmarks. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors. Various embodiments of the flow 200, or portions thereof, can be included on a semiconductor chip and implemented in special purpose logic, programmable logic, and so on. Embodiments can include defining a region of interest (ROI) in the image that includes the face; extracting one or more histogram-of-oriented-gradients (HoG) features from the ROI; and computing a set of facial metrics based on the one or more HoG features. Embodiments can further include identifying multiple human faces within the image; defining a region of interest (ROI) in the image for each identified human face; extracting one or more histogram-of-oriented-gradients (HoG) features from each ROI; and computing a set of facial metrics based on the one or more HoG features for each of the multiple human faces.

Figure 3:
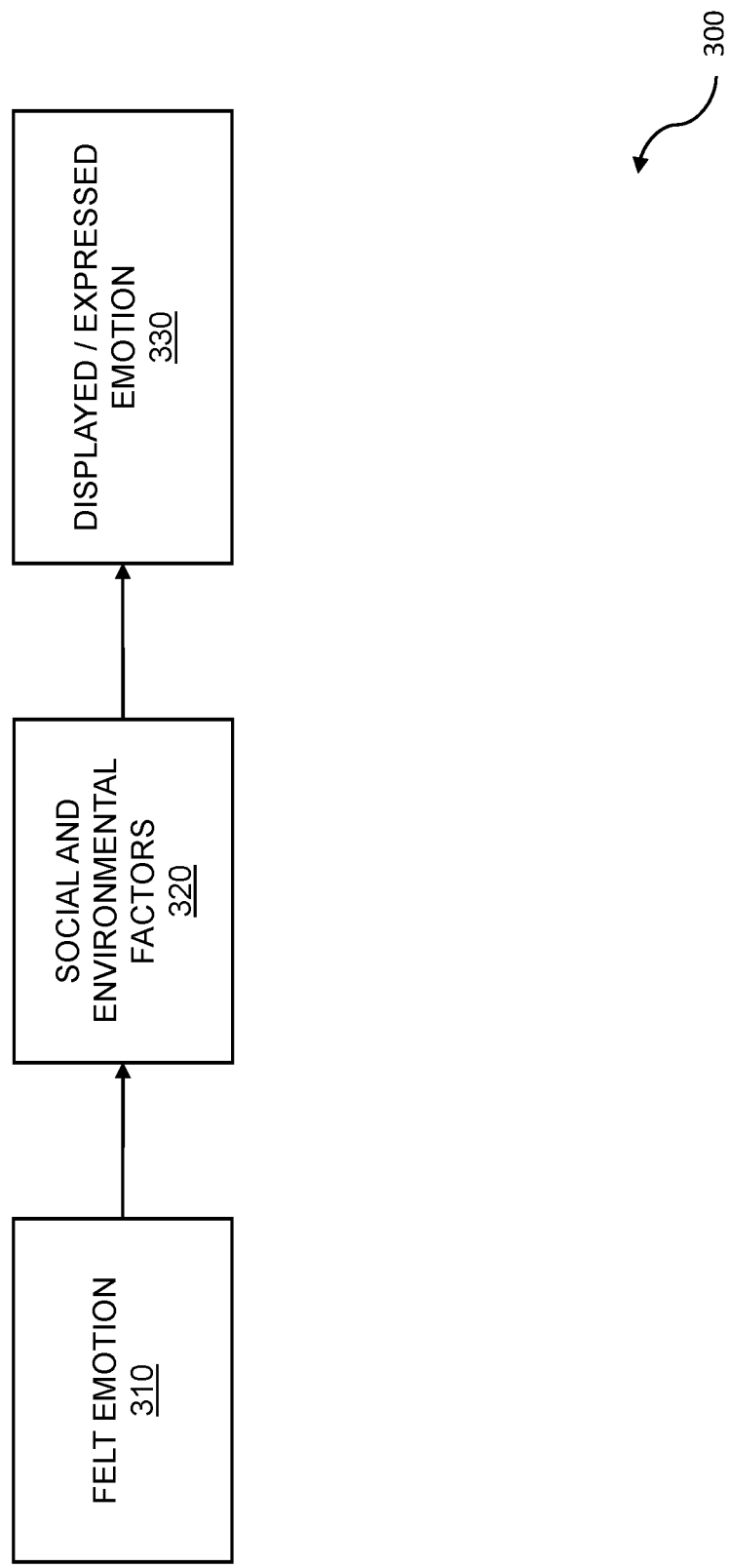
FIG. 3 is a flow diagram for emotion expression.

FIG. 3 is a flow diagram for emotion expression. The expression of various emotions can be presented on a human face and can be determined using sub-sectional components. The sub-sectional components can be used with performing the evaluation of emotional content of the face. The sub-sectional components can be used to provide a context to the emotion expression. The flow 300, or portions thereof, can be implemented on a mobile device, a server, a semiconductor chip, or another electronic device. The flow 300 includes felt emotion 310. The felt emotion can include one or more of sadness, stress, happiness, fear, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, mirth, etc. The flow 300 includes social and environmental factors 320. The social and environmental factors can include sub-sectional components of a population. The sub-sectional component can be determined based on a demographic. Any appropriate demographic can be used for the determining. The demographic can include an age, ethnicity, culture, gender, a setting, an environment, a power, a status, a time of day, a day of a week, a time of year, weather, and so on. The flow 300 includes displayed and/or expressed emotion 330. The displayed and/or expressed emotion can be interpreted by an observer of a person, for example. The displayed and/or expressed emotion, can include smiles, frowns, brow furrows, etc. The displayed and/or expressed emotion can be based on the facial action coding system (FACS).

Figure 4:
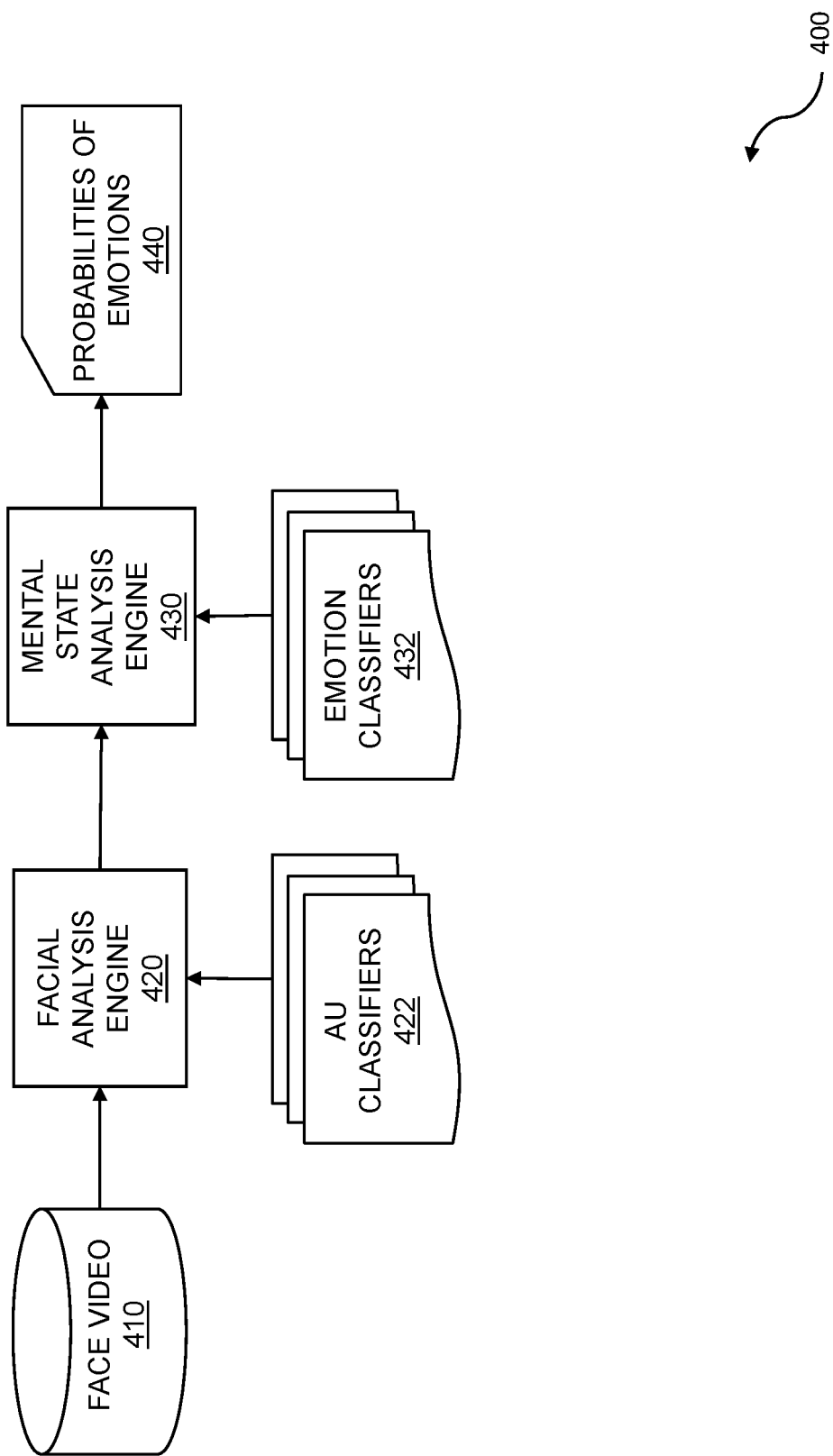
FIG. 4 is a flow diagram for probability of emotion computation.

FIG. 4 is a flow diagram for probability of emotion computation. Probabilities of one or more emotions can be determined using sub-sectional components. The sub-sectional components can be used with performing the evaluation of emotional content of the face. The sub-sectional components can be used to provide a context to the probabilities of emotions. The flow 400, or portions thereof, can be implemented on a mobile device, a server, a semiconductor chip, or another electronic device. The flow 400 includes one or more face videos 410. The videos can include images captured from a camera, where the camera can be a still camera, a video camera, and so on. The videos captured from a video camera can include video frames. The flow 400 includes a facial analysis engine 420. The facial analysis engine can be a hardware engine and/or a software engine. The facial analysis engine 420 can be implemented on a mobile device, a server, a semiconductor chip, etc. The facial analysis engine 420 can use action unit (AU) classifiers 422. The facial analysis engine 420 can perform a skin-tone analysis to assess an average skin tone/color as part of a demographic characterization. The facial analysis engine 420 can further utilize the shape of facial features such as eyes, nose, jaw, and/or neck to determine an ethnicity and/or gender. Any number of action unit classifiers can be used. The action unit classifiers can be used to identify one or more action units, including actions units from the facial action coding system (FACS). In various cases, the action units can be used to identify an inner brow raiser (AU1), a nose wrinkler (AU9), and so on. Any number of action units can be identified by the facial analysis engine using AU classifiers. The flow 400 includes a mental state analysis engine 430. The mental state analysis engine 430 can be implemented on a mobile device, a server, a semiconductor chip, and so on. The mental state analysis engine 430 can be used to determine any number of mental states. The mental state analysis engine 430 can use emotion classifiers 432. The emotion classifiers 432 can be used to identify one or more emotions, including, but not limited to, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, mirth, etc. The flow 400 includes probabilities of emotions 440. The probabilities of emotions can indicate the probability that one or more emotions can be present in the face video. For example, the probabilities of emotions can indicate that the probability of happiness is 40%, the probability of engagement is 35%, and the probability of trust is 45%. Any number of probabilities of emotions can be included. The probabilities can include a percentage, a value between 0 and 1, etc.

Figure 5:
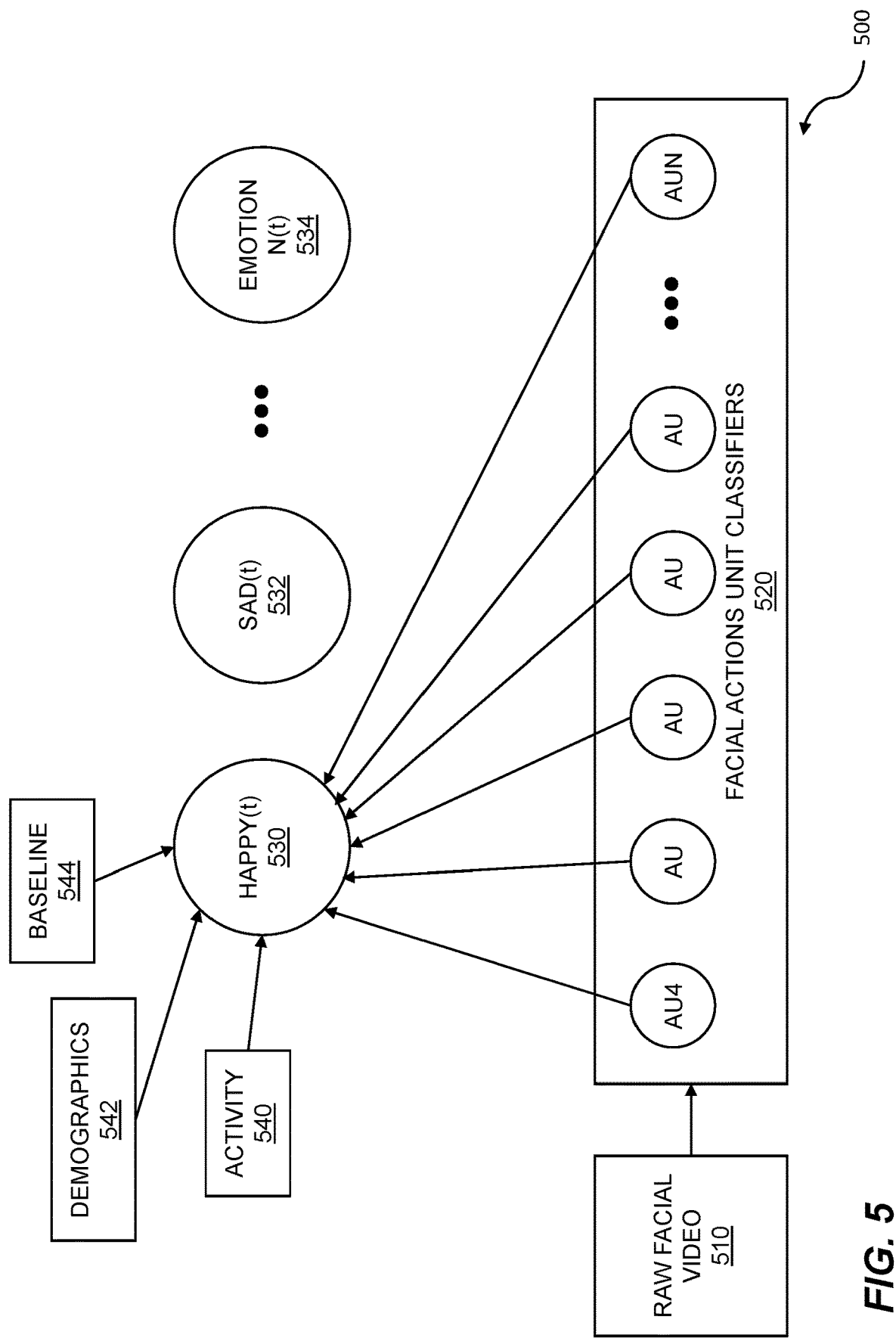
FIG. 5 is a flow diagram for result determination.

FIG. 5 is a flow diagram for result determination. Result determination can be performed using sub-sectional components. The sub-sectional components can be used with performing the evaluation of emotional content of the face. The sub-sectional components can be used to provide a context to the result determination. The flow 500, or portions thereof, can be implemented on a mobile device, a server, a semiconductor chip, or another electronic device. The flow 500 includes raw facial video 510. The facial video 510 can include still images, frames from a video, a video, and so on. The flow 500 includes facial action unit (AU) classifiers 520. One or more facial action unit classifiers, AU4 to AUN, can be used for determining facial actions. For example, the facial action unit classifiers can include brow lowerer (AU4), upper lip raiser (AU10), etc. The facial action unit classifiers can be applied to the raw facial video 510 to determine moods, emotions, mental states, content of the face, and so on. In embodiments, performing the evaluation of content of the face includes evaluation of action units for the content of the face. The content of the face can change over time. Facial content can include happy(t) 530, sad(t) 532, an emotion N(t) 534, and so on. So, at a first time t1 in a raw facial video, the content of the face can be happy(t1); at a second time t2, the content of the face can be sad(t2); at a time $t_N$, the content of the face can be emotion $n(t_N)$; and so on. Multiple content types can be determined. Determining of the content of the face can be based on evaluating of the individual to be within a sub-sectional component of a population. Resulting facial content can depend on a sub-sectional component of a population into which a person falls. Thus, depending on a sub-sectional component of a population into which a person falls can further define content of a face. The sub-sectional component of a population can be used in disambiguating among a plurality of content types for the content of the face based on the sub-sectional component of a population. The disambiguating can include performing analysis that is based on a baseline 544 for a specific individual, on demographics 542, on activity 540 of the person, and so on. The disambiguating can be based on experiential context for an individual. The experiential context of the individual can include a baseline 544 from one or more previous experiences. The sub-sectional component can be determined based on a demographic 542. The demographic can include an age, ethnicity, culture, gender, and so on. The sub-sectional component can be determined based on an activity 540 in which the individual is participating. In some cases, if the individual is reading a humorous passage in a book, their reaction to the humorous passage can be a smile or a quiet chuckle, while the same individual viewing a comedic movie or television program can react with a broad open-lipped smile, by laughing out loud, and so on. The activity could include a computer game, an electronic game, an interpersonal game, reading a book, reading an eBook, watching a media presentation, and so on. The activity could be considered a social function, and thus a social component could influence a resulting expression of an emotion. Different activities could have different norms for expressiveness: for quieter activities, a subtle expression could communicate a similar emotion to a more pronounced expression that occurs during a louder activity. Note that for the sake of drawing clarity, the baseline 544, demographics 542, and activity 540 are only shown for happy 530, but each emotion has similar elements connected in a similar manner.

Figure 6:
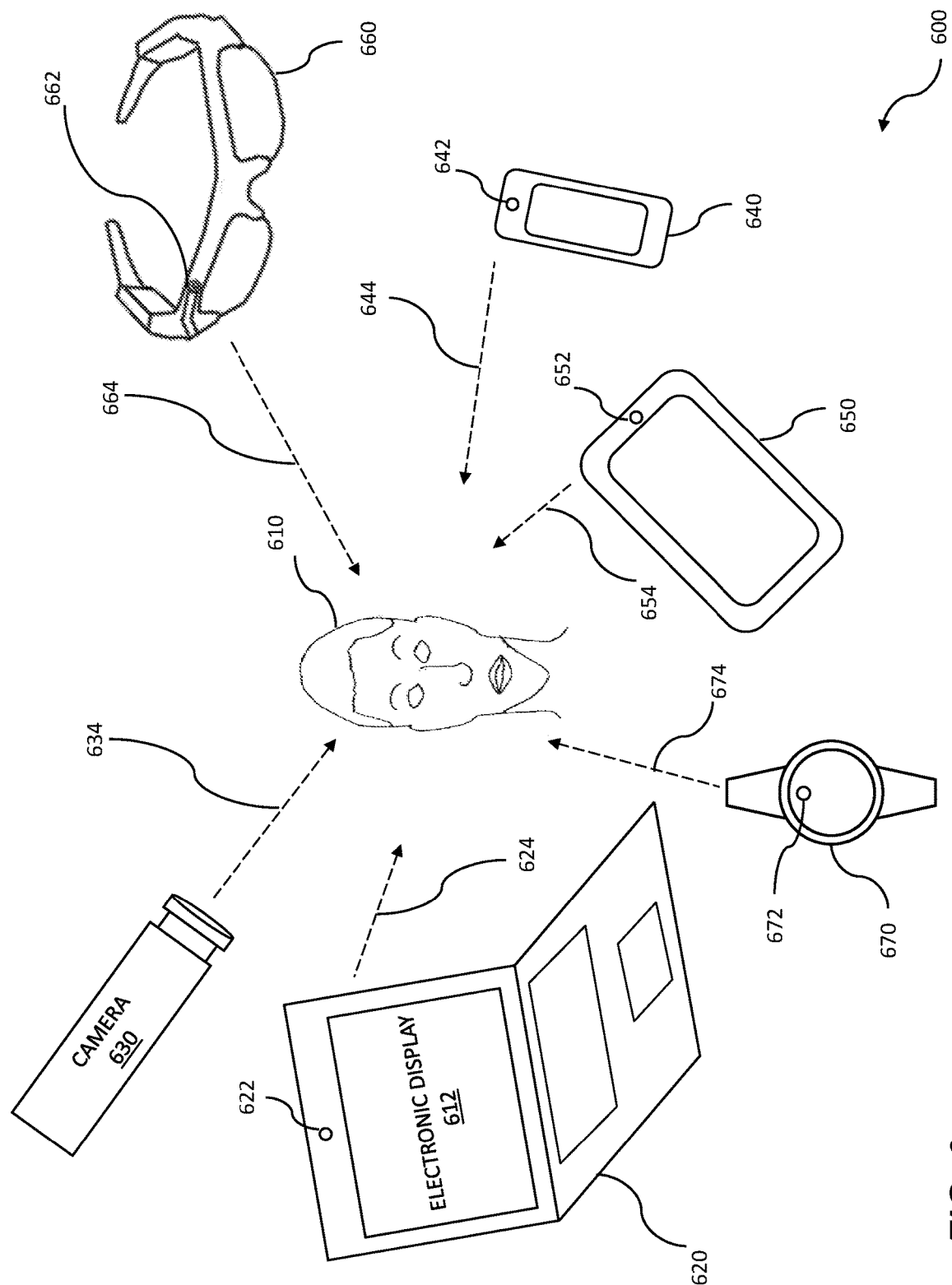
FIG. 6 is a diagram showing image collection including multiple mobile devices.

FIG. 6 is a diagram showing image collection including multiple mobile devices. The collected images can be evaluated for an individual to be within a sub-sectional component of a population. The sub-sectional components can be used with performing the evaluation of content of the face. The sub-sectional components can be used to provide a context. In the diagram 600, the multiple mobile devices can be used singly or together to collect video data on a user 610. While one person is shown, the video data can be collected on any number of people. A user 610 can be observed as she or he is performing a task, experiencing an event, viewing a media presentation, and so on. The user 610 can be shown one or more media presentations, political presentations, or social media, or another form of displayed media. The one or more media presentations can be shown to a plurality of people. The media presentations can be displayed on an electronic display 612 or another display. The data collected on the user 610 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 610 can be analyzed and viewed for a variety of purposes including expression analysis, mental state analysis, and so on. The electronic display 612 can be on a laptop computer 620 as shown, a tablet computer 650, a cell phone 640, a television, a mobile monitor, or any other type of electronic device. In one embodiment, expression data is collected on a mobile device such as a cell phone 640, a tablet computer 650, a laptop computer 620, or a watch 670. Thus, the multiple sources can include at least one mobile device, such as a phone 640 or a tablet 650, or a wearable device such as a watch 670 or glasses 660. A mobile device can include a forward-facing camera and/or a rear-facing camera that can be used to collect expression data. Sources of expression data can include a webcam 622, a phone camera 642, a tablet camera 652, a wearable camera 662, and a mobile camera 630. A wearable camera can comprise various camera devices such as the watch camera 672.

As the user 610 is monitored, the user 610 might move due to the nature of the task, boredom, discomfort, distractions, or for another reason. As the user moves, the camera with a view of the user's face can be changed. Thus, as an example, if the user 610 is looking in a first direction, the line of sight 624 from the webcam 622 is able to observe the user's face, but if the user is looking in a second direction, the line of sight 634 from the mobile camera 630 is able to observe the user's face. Furthermore, in other embodiments, if the user is looking in a third direction, the line of sight 644 from the phone camera 642 is able to observe the user's face, and if the user is looking in a fourth direction, the line of sight 654 from the tablet camera 652 is able to observe the user's face. If the user is looking in a fifth direction, the line of sight 664 from the wearable camera 662, which can be a device such as the glasses 660 shown and can be worn by another user or an observer, is able to observe the user's face. If the user is looking in a sixth direction, the line of sight 674 from the wearable watch-type device 670, with a camera 672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 610 can also use a wearable device, including a camera, for gathering contextual information and/or collecting expression data on other users. Because the user 610 can move her or his head, the facial data can be collected intermittently when she or he is looking in a direction of a camera. In some cases, multiple people can be included in the view from one or more cameras, and some embodiments include filtering out faces of one or more other people to determine whether the user 610 is looking toward a camera. All or some of the expression data can be continuously or sporadically available from the various devices and other devices.

The captured video data can include facial expressions and can be analyzed on a computing device such as the video capture device or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 7:
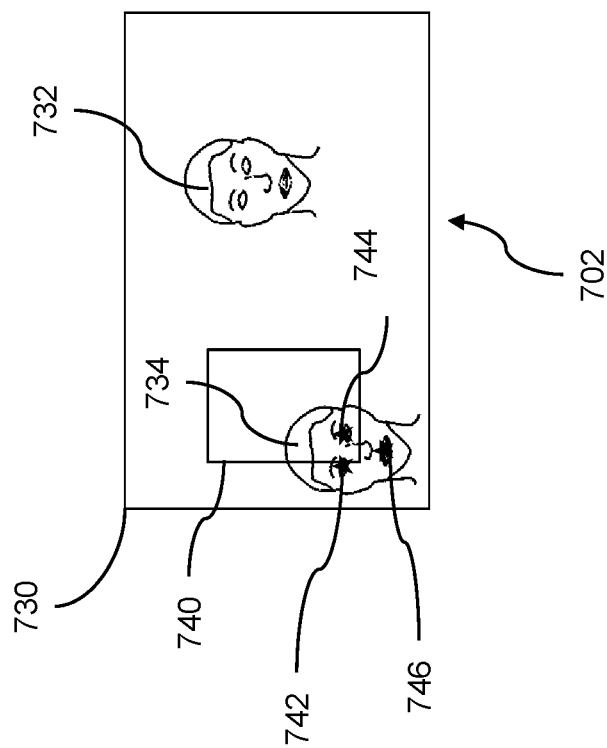
FIG. 7 illustrates feature extraction for multiple faces.
Figure 7:
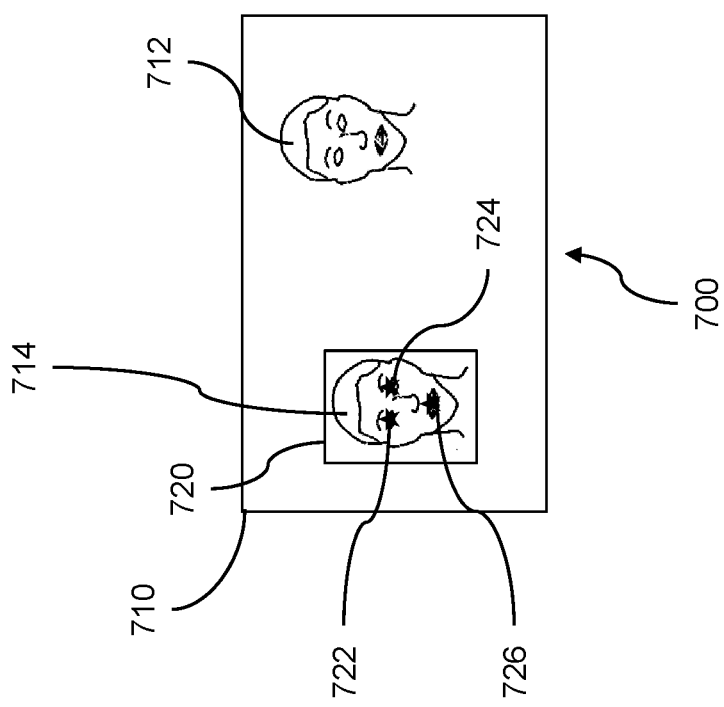

FIG. 7 illustrates feature extraction for multiple faces. Features of a face or a plurality of faces can be extracted from collected video data. Feature extraction for multiple faces can be based on sub-sectional components. The sub-sectional components can be used with performing the evaluation of content of the face. The sub-sectional components can be used to provide a context. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types such as numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. The classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 7, the detection of the first face, the second face, and any number of faces can include identifying facial landmarks, generating a bounding box, and prediction of a bounding box and landmarks for a next frame, where the next frame can be one of a plurality of frames of a video containing faces. A first video frame 700 includes a frame boundary 710, a first face 712, and a second face 714. The video frame 700 also includes a bounding box 720. Facial landmarks can be generated for the first face 712. Face detection can be performed to initialize a second set of locations for a second set of facial landmarks for a second face within the video. Facial landmarks in the video frame 700 can include the facial landmarks 722, 724, and 726. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 720. Bounding boxes can also be estimated for one or more other faces within the boundary 710. The bounding box can be refined, as can one or more facial landmarks. The refining of the second set of locations for the second set of facial landmarks can be based on localized information around the second set of facial landmarks. The bounding box 720 and the facial landmarks 722, 724, and 726 can be used to estimate future locations for the second set of locations for the second set of facial landmarks in a future video frame from the first video frame.

A second video frame 702 is also shown. The second video frame 702 includes a frame boundary 730, a first face 732, and a second face 734. Embodiments include tracking the face within the video. Furthermore, embodiments include tracking a second face within the video. The second video frame 702 also includes a bounding box 740 and the facial landmarks 742, 744, and 746. In other embodiments, any number of facial landmarks are generated and used for facial tracking of the two or more faces of a video frame, such as the shown second video frame 702. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 740 can be estimated, where the estimating can be based on the location of the generated bounding box 720 shown in the first video frame 700. The three facial points shown, facial points 742, 744, and 746, might lie within the bounding box 740 or might not lie partially or completely within the bounding box 740. For instance, the second face 734 might have moved between the first video frame 700 and the second video frame 702. Based on the accuracy of the estimating of the bounding box 740, a new estimation can be determined for a third, future frame from the video, and so on. The evaluation can be performed, all or in part, on semiconductor based logic. In embodiments, evaluation of content of the face is based on motion of regions within the face. Each video frame can be considered as an image. In embodiments, the image is one image from a series of images of the individual. Thus, in embodiments, there is a series of images. In embodiments, the series of images comprises a video of the individual.

Figure 8:
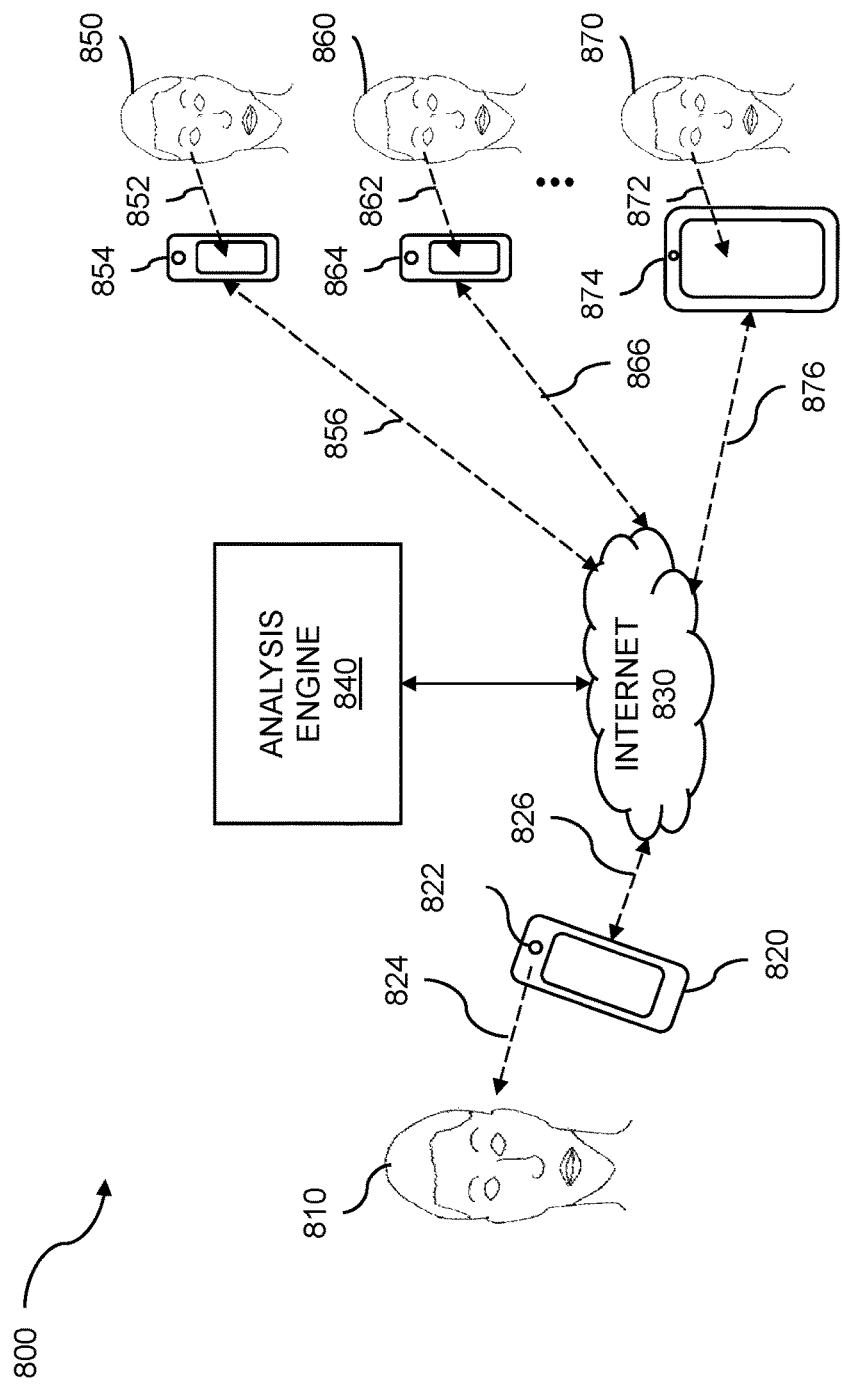
FIG. 8 shows live streaming of social video.

FIG. 8 shows live streaming of social video. A video of a person or people can be transmitted via live streaming. The live streaming of social video can be based on sub-sectional components. The sub-sectional components can be used to provide a context. The streaming and analysis can be facilitated by a video capture device, a local server, a remote server, a semiconductor based logic, and so on. The streaming can be live streaming and can include mental state analysis, mental state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcasted as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 800 shows a user 810 broadcasting a video live stream to one or more people as shown by the person 850, the person 860, and the person 870. A portable, network-enabled electronic device 820 can be coupled to a forward-facing camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The captured video can be sent to an analysis or recommendation engine 840 using a network link

826 to the Internet 830. The network link can be a wireless link, a wired link, and so on. The recommendation engine 840 can recommend to the user 810 an app and/or platform that can be supported by the server and can be used to provide a video live-stream to one or more followers of the user 810. In the example 800, the user 810 has three followers: the person 850, the person 860, and the person 870. Each follower has a line-of-sight view to a video screen on a portable, networked electronic device. In other embodiments, one or more followers follow the user 810 using any other networked electronic device, including a computer. In the example 800, the person 850 has a line-of-sight view 852 to the video screen of a device 854; the person 860 has a line-of-sight view 862 to the video screen of a device 864, and the person 870 has a line-of-sight view 872 to the video screen of a device 874. The portable electronic devices 854, 864, and 874 can each be a smartphone, a PDA, a tablet, and so on. Each portable device can receive the video stream being broadcasted by the user 810 through the Internet 830 using the app and/or platform that can be recommended by the recommendation engine 840. The device 854 can receive a video stream using the network link 856, the device 864 can receive a video stream using the network link 866, the device 874 can receive a video stream using the network link 876, and so on. The network link can be a wireless link, a wired link, a hybrid link, and so on. Depending on the app and/or platform that can be recommended by the recommendation engine 840, one or more followers, such as the followers 850, 860, 870, and so on, can reply to, comment on, and otherwise provide feedback to the user 810 using their devices 854, 864, and 874, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the observed person. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made regarding the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor based logic.

Figure 9:
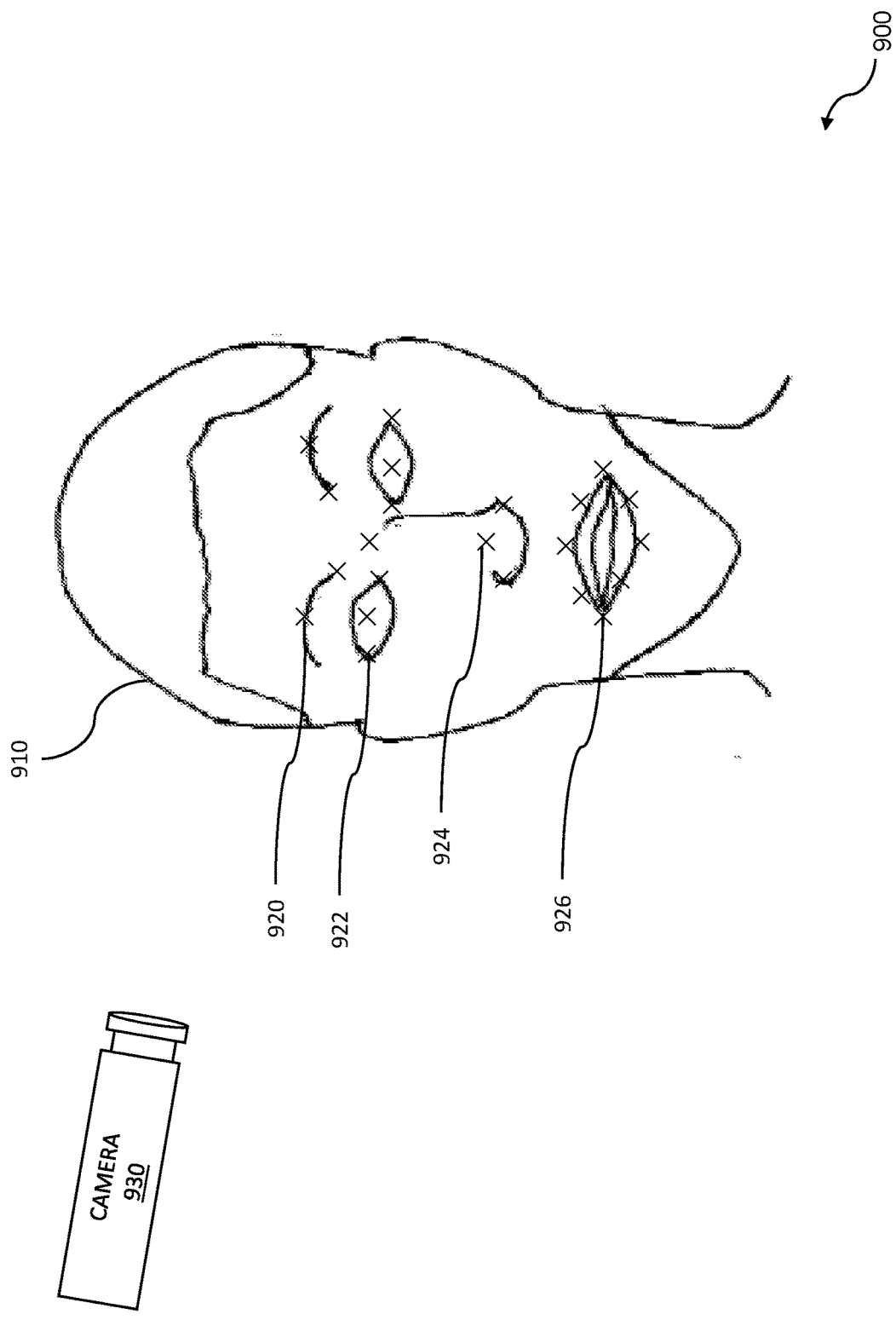
FIG. 9 shows example facial data collection including landmarks.

FIG. 9 shows example facial data collection including landmarks. In the example 900, facial data including facial landmarks can be collected using a variety of electronic hardware and software techniques. The collecting of facial data including landmarks can be based on sub-sectional components of a population. The sub-sectional components can be used with performing the evaluation of content of the face, identifying facial landmarks, etc. The sub-sectional components can be used to provide a context. A face 910 can be observed using a camera 930 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 930 relative to the face 910, the number of cameras used, the illumination of the face, etc. In some cases, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures) with all the analysis being accomplished or augmented by a mobile device, a server, semiconductor-based logic, and so on. Thus, embodiments include performing facial landmark detection on the face of the individual.

Figure 10:
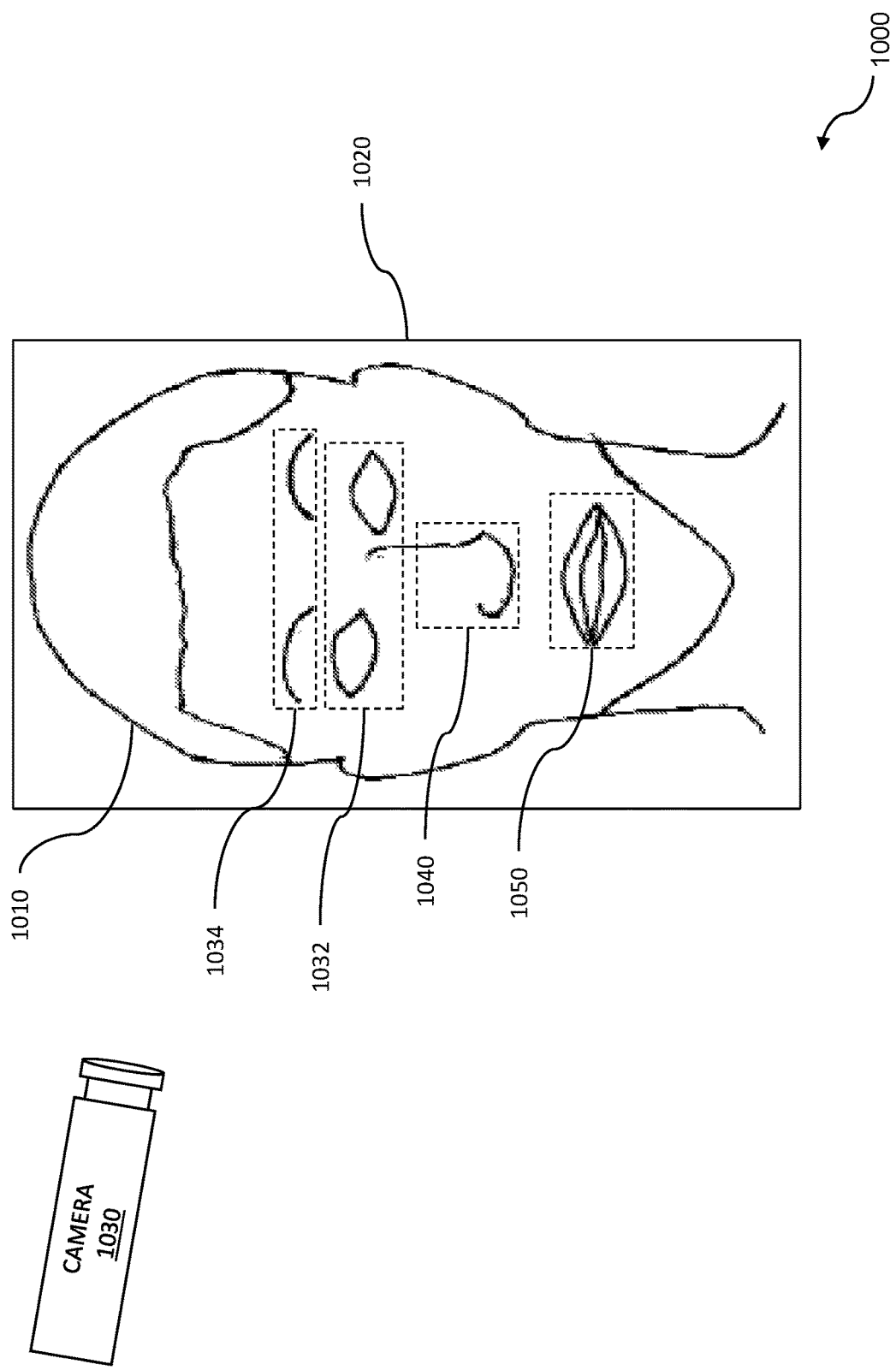
FIG. 10 shows example facial data collection including regions.

FIG. 10 shows example facial data collection including regions. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, estimate, etc. mental states, emotions, and so on of a person from whom facial data can be collected. The one or more emotions that are determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1000, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1010 can be observed using a camera 1030, a sensor, a combination of cameras and/or sensors, and so on. The camera 1030 can be used to collect facial data that can be used to determine that a face is present in an image. When a face is present in an image, a bounding box 1020 can be placed around the face. Placement of the bounding box around the face can be based on detection of facial landmarks. The camera 1030 can be used to collect from the bounding box 1020 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1030 relative to the face 1010, the number of cameras and/or sensors used, the illumination of the face, any obstructions to viewing the face, and so on.

The facial regions that can be collected by the camera 1030, sensor, or combination of cameras and/or sensors can include any of a variety of facial features. The facial features that can be included in the facial regions that are collected can include eyebrows 1034, eyes 1032, a nose 1040, a mouth 1050, ears, hair, texture, tone, and so on. Any number of facial features can be included in any number of facial regions. Thus, embodiments include extracting features within the face of the individual.

The facial regions can be analyzed to determine facial expressions including probabilities of facial expressions. In embodiments, classifiers are used for the analysis. The classifiers can include algorithms, heuristics, code segments, and so on that can be used for the analysis. For example, consider facial features that can include the eyebrows 1034. One or more classifiers can be used to analyze the facial regions that can include the eyebrows to determine a probability for either a presence or an absence of an eyebrow furrow. The presence of an eyebrow furrow can indicate the person from whom the facial data can be collected is annoyed, confused, unhappy, and so on. In another example, consider facial features can include a mouth 1050. One or more classifiers can be used to analyze the facial region that can include the mouth to determine a probability for either a presence or an absence of mouth edges turned up to form a smile. Any number of classifiers can be used to determine one or more facial expressions.

Figure 11:
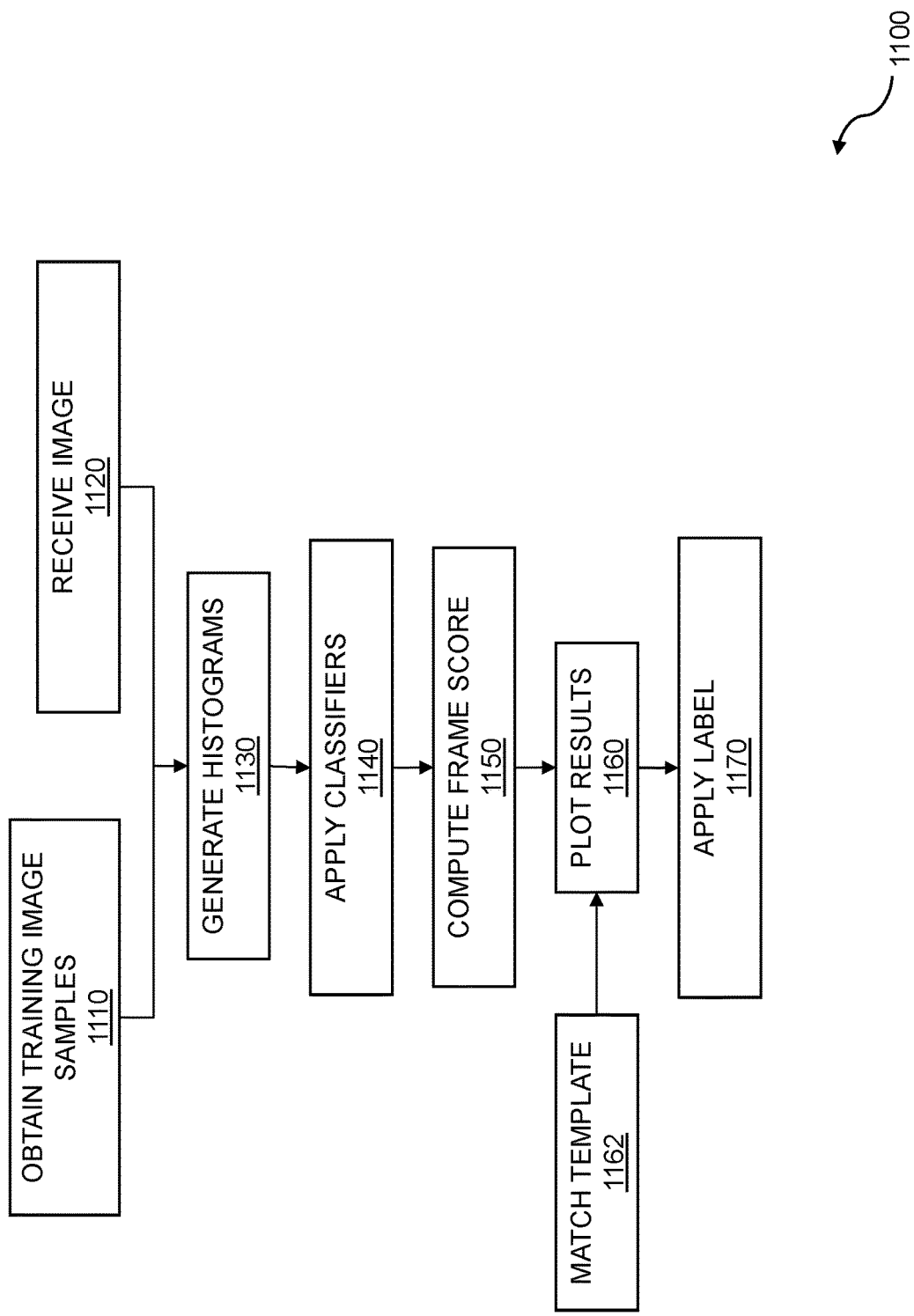
FIG. 11 is a flow diagram for detecting facial expressions that can be used for analysis based on sub-sectional components.

FIG. 11 is a flow diagram for detecting facial expressions that can be used for analysis based on sub-sectional components. The sub-sectional components can be used with performing the detecting facial expressions. The sub-sectional components can be used to provide a context. The flow 1100, or portions thereof, can be implemented in semiconductor logic, can be accomplished using a mobile device, can be accomplished using a server device, and so on. The flow 1100 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk. In embodiments, image classifiers are used to map facial landmarks within the face to emotional content.

The flow 1100 begins by obtaining training image samples 1110. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1100 continues with receiving an image 1120. The image 1120 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1100 continues with generating histograms 1130 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1100 continues with applying classifiers 1140 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1100 continues with computing a frame score 1150. The score computed for an image, where the image can be a frame from a video, can be used to determine the presence of a facial expression in the image or video frame. The score can be based on one or more versions of the image 1120 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1100 continues with plotting results 1160. The results that are plotted can include one or more scores for one or more frames computed over a given time t. For example, the plotted results can include classifier probability results from analysis of HoGs for a sequence of images and video frames. The plotted results can be matched with a template 1162. The template can be temporal and can be represented by a centered box function or another function. A best fit with one or more templates can be found by computing a minimum error. Other best-fit techniques can include polynomial curve fitting, geometric curve fitting, and so on. The flow 1100 continues with applying a label 1170. The label can be used to indicate that a particular facial expression has been detected in the one or more images or video frames which constitute the image that was received 1120. The label can be used to indicate that any of a range of facial expressions has been detected, including a smile, an asymmetric smile, a frown, and so on. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
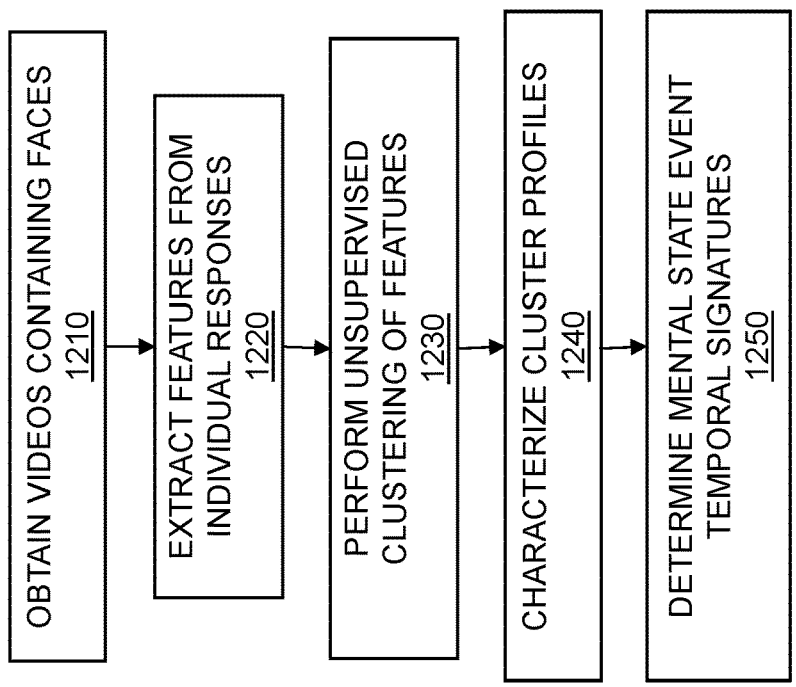
FIG. 12 is a flow diagram for the large-scale clustering of facial events.

FIG. 12 is a flow diagram for the large-scale clustering of facial events that can be used in conjunction with analysis using sub-sectional components. The sub-sectional components can be used with performing the evaluation of content of the face. The sub-sectional components can be used to provide a context. The clustering and evaluation of facial events can be augmented using a mobile device, a server, semiconductor based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on.

The flow 1200 begins with obtaining videos containing faces 1210. The videos can be obtained using one or more cameras, where the cameras can include a webcam coupled to one or more devices employed by the one or more people using the web-based framework. The flow 1200 continues with extracting features from the individual responses 1220. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1200 continues with performing unsupervised clustering of features 1230. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1200 continues with characterizing cluster profiles 1240. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on.

The flow 1200 continues with determining metal state event temporal signatures 1250. The mental state event temporal signature can provide information about how the mental state of an individual may change over time. The change in mental state can be triggered by an event such as a humorous video, surprise movie ending, or the like. The mental state event temporal signatures can include information on rise time to facial expression intensity, fall time from facial expression intensity, duration of a facial expression, and so on. In some embodiments, the mental state event temporal signatures are associated with sub-sectional components that may include certain demographics, ethnicities, cultures, etc. The mental state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

In some embodiments, the mental state event temporal signatures are associated with sub-sectional components that are experiential. This can include a setting. A setting can have a variety of attributes. Attributes include average sound level, average light level, and/or a crowd factor. People can react differently depending on an experiential setting. As an example, a person watching television alone at home might react to something humorous with a mild smile, while a person watching the same content in a movie theater with a crowd might react with a more intense smile or laughter based in part on the surrounding crowd. Thus, these sub-sectional components can provide important data for compensating based on content type intensity. Referring again to the example, while in a movie theater surrounded by a crowd of laughing people, an individual might be inclined to express a more intense smile or laugh than if they were viewing at home alone watching on a television or computer. Therefore, a high-intensity laugh can mean more coming from a person in a solitary environment than for a similar expression in a large group environment. By accounting for such sub-sectional components, a greater level of granularity and accuracy in assessing the effectiveness of media content can be achieved. Thus, in embodiments, the disambiguating is further based on experiential context for the individual. Various steps in the flow 1200 may be changed in order, repeated, omitted, or the like without departing from the disclosed concepts. Various embodiments of the flow 1200 can be included in a computer program product embodied in a non-transitory computer readable medium that includes code executable by one or more processors. Various embodiments of the flow 1200, or portions thereof, can be included on a semiconductor chip and implemented in special purpose logic, programmable logic, and so on.

Figure 13:
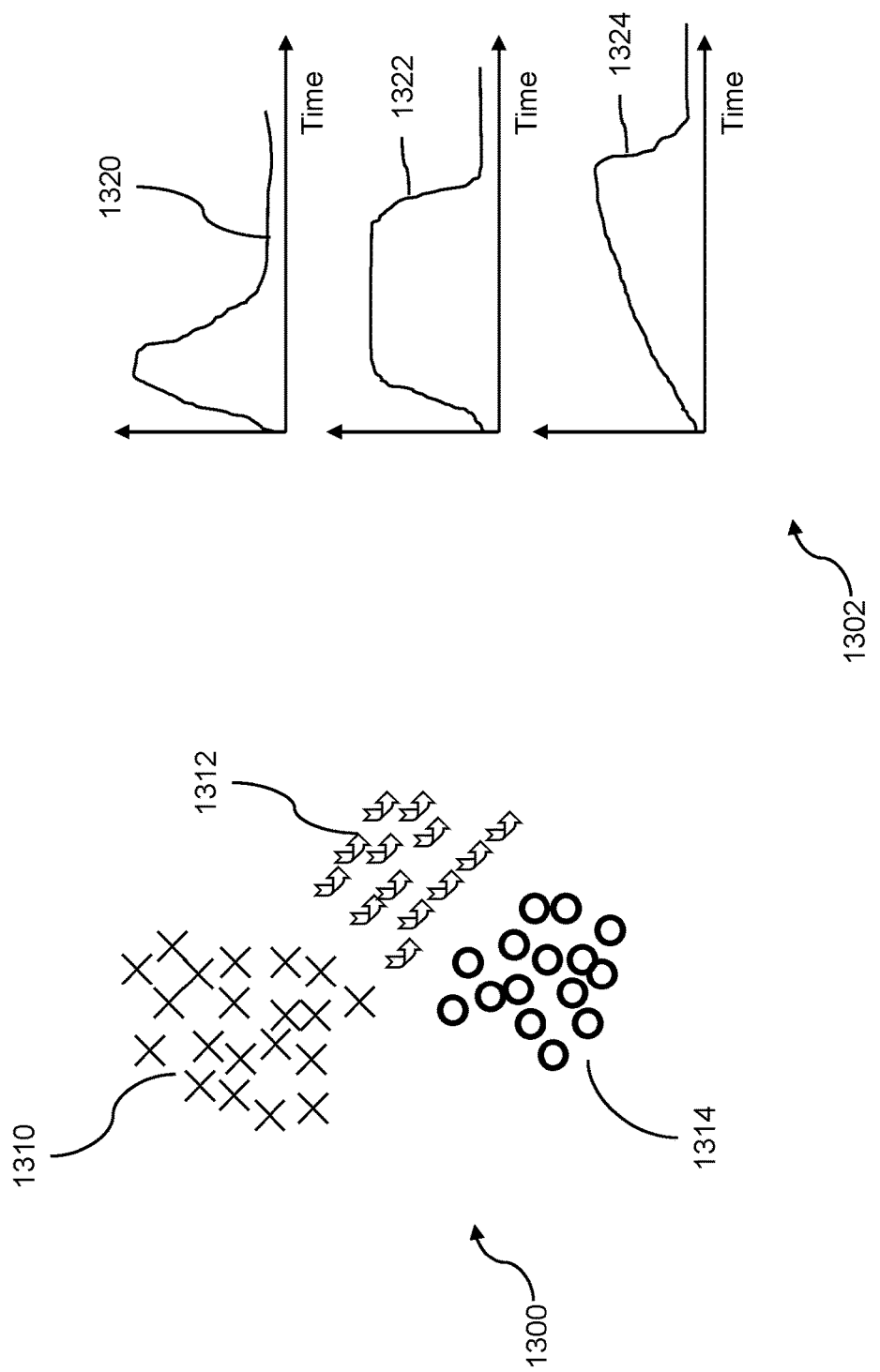
FIG. 13 shows unsupervised clustering of features and characterizations of cluster profiles.

FIG. 13 shows unsupervised clustering of features and characterizations of cluster profiles that can be used for analysis using sub-sectional components. The sub-sectional components can be used with performing the evaluation of content of the face. The sub-sectional components can be used to provide a context. Features including samples of facial data can be clustered using unsupervised clustering. Various clusters can be formed which include similar groupings of facial data observations. The example 1300 shows three clusters, clusters 1310, 1312, and 1314. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information (demographic), where the demographic information can include educational level, geographic location, age, gender, income level, and so on. In embodiments, the sub-sectional component is determined based on a demographic. In embodiments, the demographic includes an age, ethnicity, culture, or gender.

The cluster profiles 1302 can be generated based on the clusters that can be formed from unsupervised clustering, with time shown on the x-axis and intensity or frequency shown on the y-axis. The cluster profiles can be based on captured facial data including facial expressions. The cluster profile 1320 can be based on the cluster 1310, the cluster profile 1322 can be based on the cluster 1312, and the cluster profile 1324 can be based on the cluster 1314. The cluster profiles 1320, 1322, and 1324 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 14A:
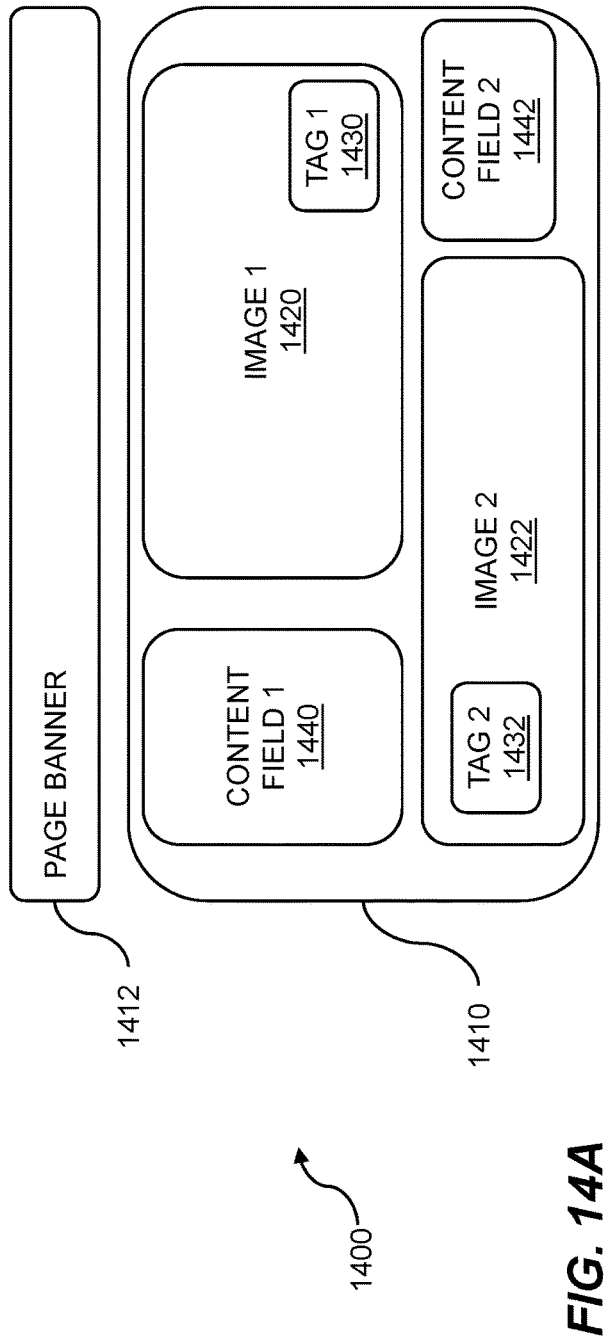
FIG. 14A shows example tags embedded in a webpage.

FIG. 14A shows example tags embedded in a webpage. The webpage can contain analysis using sub-sectional components. The sub-sectional components can be used with performing the evaluation of content of a face. The sub-sectional components can be used to provide a context. Once a tag is detected, a mobile device, a server, semiconductor based logic, etc. can be used to evaluate associated facial expressions. A webpage 1400 can include a page body 1410, a page banner 1412, and so on. The page body can include one or more objects, where the objects can include text, images, videos, audio, and so on. The example page body 1410 shown includes a first image, image 1 1420; a second image, image 2 1422; a first content field, content field 1 1440; and a second content field, content field 2 1442. In practice, the page body 1410 can contain any number of images and content fields, and can include one or more videos, one or more audio presentations, and so on. The page body can include embedded tags, such as tag 1 1430 and tag 2 1432. In the example shown, tag 1 1430 is embedded in image 1 1420, and tag 2 1432 is embedded in image 2 1422. In embodiments, any number of tags are imbedded. Tags can also be imbedded in content fields, in videos, in audio presentations, etc. When a user mouses over a tag or clicks on an object associated with a tag, the tag can be invoked. For example, when the user mouses over tag 1 1430, tag 1 1430 can then be invoked. Invoking tag 1 1430 can include enabling a camera coupled to a user's device and capturing one or more images of the user as the user views a media presentation (or digital experience). In a similar manner, when the user mouses over tag 2 1432, tag 2 1432 can be invoked. Invoking tag 2 1432 can also include enabling the camera and capturing images of the user. In other embodiments, other actions are taken based on invocation of the one or more tags. Invoking an embedded tag can initiate an analysis technique, post to social media, award the user a coupon or another prize, initiate mental state analysis, perform emotion analysis, and so on.

Figure 14B:
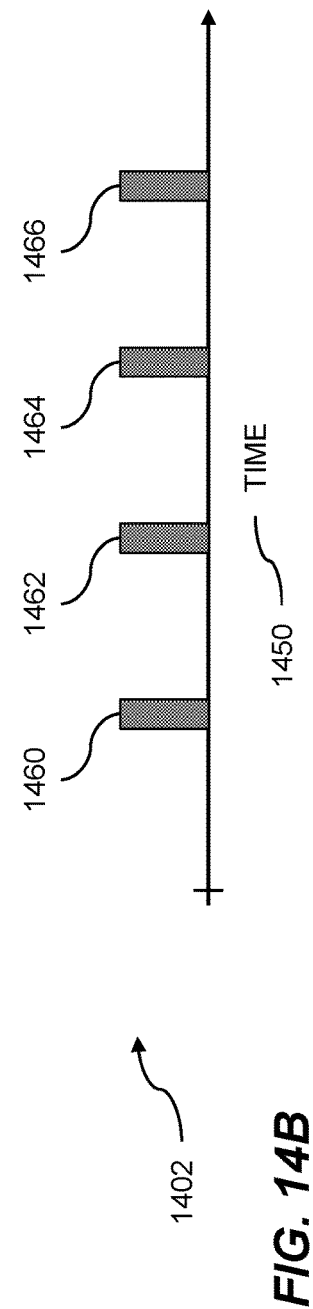
FIG. 14B shows invoking tags to collect images.

FIG. 14B shows invoking tags to collect images. The tags can be related to analysis using sub-sectional components. The sub-sectional components can be used with performing the evaluation of content of a face. The sub-sectional components can be used to provide a context. As previously stated, a media presentation can be a video, a webpage, and so on. A video 1402 can include one or more embedded tags, such as a tag 1460, another tag 1462, a third tag 1464, a fourth tag 1466, and so on. In practice, any number of tags can be included in the media presentation. The one or more tags can be invoked during the media presentation. The collection of the invoked tags can occur over time, as represented by a timeline 1450. When a tag is encountered in the media presentation, the tag can be invoked. When the tag 1460 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1460 does not enable the camera nor capture images of the user during the media presentation. The user can indicate an opt-in for certain types of participation, where opting-in can be dependent on specific content in the media presentation. The user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags imbedded in the media presentation that are related to advertisements would not enable the camera when invoked. Various other situations of tag invocation are possible.

Figure 15:
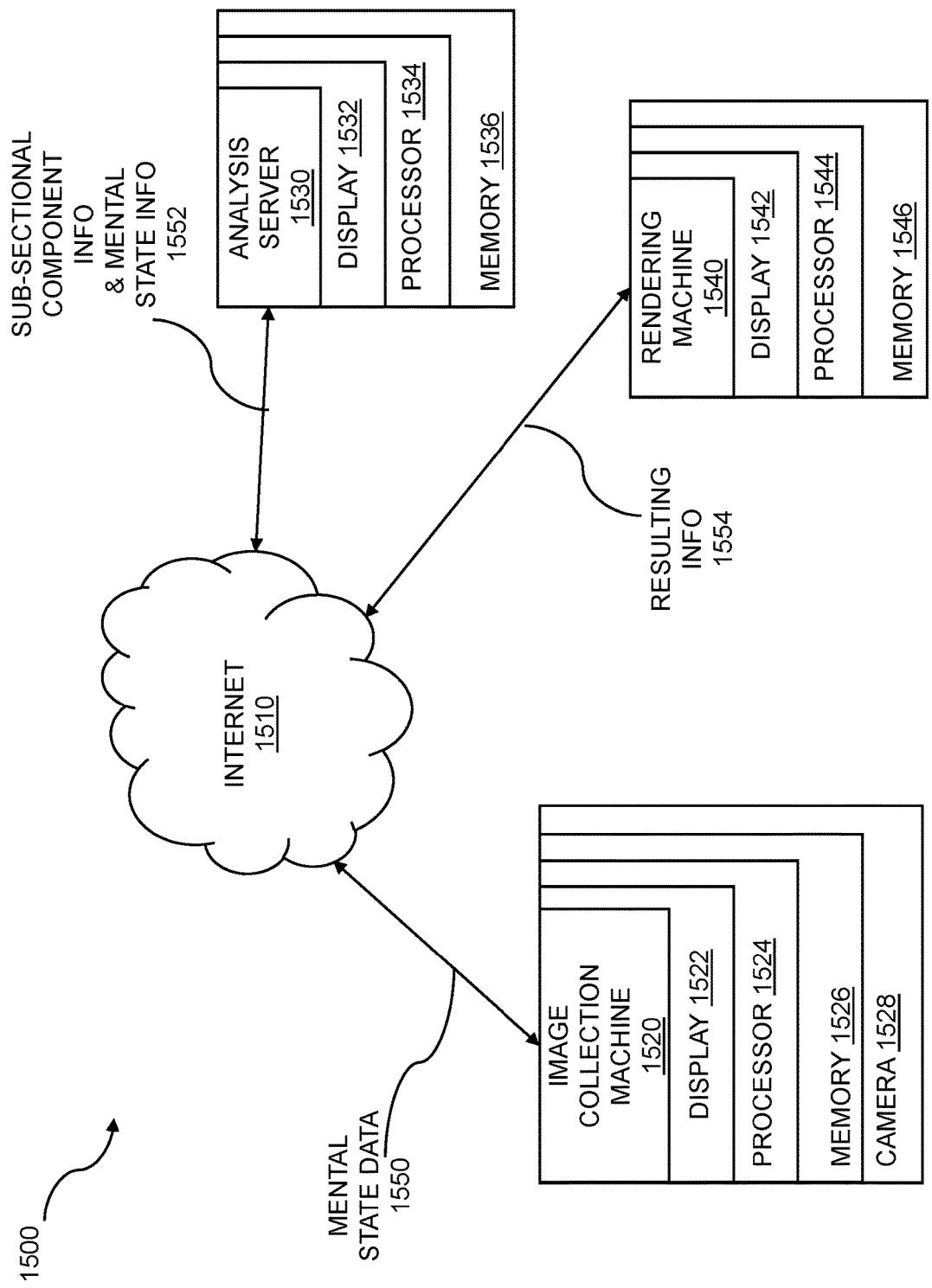
FIG. 15 is a system diagram for analysis using sub-sectional components.

FIG. 15 is a system diagram for analysis using sub-sectional components. The sub-sectional components can be used with performing the evaluation of content of the face. The sub-sectional components can be used to provide a context. The system 1500 for analysis using sub-sectional component evaluation can be implemented using a variety of electronic hardware and software techniques. For example, the system 1500 for analysis using sub-sectional component evaluation can be implemented using one or more machines. An example system 1500 is shown for image collection, image analysis, and rendering. The system 1500 can include a memory which stores instructions; one or more processors attached to the memory wherein the one or more processors, when executing the instructions which are stored, are configured to: obtain an image of an individual; identify a face of the individual; evaluate the individual to be within a sub-sectional component of a population; and perform an evaluation of content of the face based on the evaluating of the individual to be within the sub-sectional component of the population.

The system 1500 can perform a computer-implemented method for image analysis comprising: obtaining an image of an individual; identifying a face of the individual; evaluating the individual to be within a sub-sectional component of a population; and performing, using one or more processors, an evaluation of content of the face based on the evaluating of the individual to be within the sub-sectional component of the population.

The system 1500 can include one or more image data collection machines 1520 linked to an analysis server 1530 and a rendering machine 1540 via the Internet 1510 or another computer network. The network can be wired or wireless, a combination of wired and wireless networks, and so on. Sub-sectional component information and mental state information 1552 can be transferred to the analysis server 1530 through the Internet 1510, for example. The example image data collection machine 1520 shown comprises one or more processors 1524 coupled to a memory 1526 which can store and retrieve instructions, a display 1522, and a camera 1528. The camera 1528 can include a webcam, a video camera, a still camera, a thermal imager, a CCD device, a phone camera, a three-dimensional camera, a depth camera, a light field camera, multiple webcams used to show different views of a person, or any other type of image capture technique that can allow captured data to be used in an electronic system. The memory 1526 can be used for storing instructions, image data on a plurality of people, one or more classifiers, one or more actions units, and so on. The display 1522 can be any electronic display, including but not limited to, a computer display, a laptop screen, a net-book screen, a tablet computer screen, a smartphone display, a mobile device display, a remote with a display, a television, a projector, or the like. Mental state data 1550 can be transferred via the Internet 1510 for a variety of purposes including analysis, rendering, storage, cloud storage, sharing, social sharing, and so on.

The analysis server 1530 can include one or more processors 1534 coupled to a memory 1536 which can store and retrieve instructions, and it can also include a display 1532. The analysis server 1530 can receive the sub-sectional component information and mental state information 1552 and analyze the image data using classifiers, action units, and so on. The classifiers and action units can be stored in the analysis server, loaded into the analysis server, provided by a user of the analysis server, and so on. The analysis server 1530 can use image data received from the image data collection machine 1520 to produce resulting information 1554. The resulting information can include emotion, mood, mental state, etc., and can be based on the sub-sectional component or components of a population. In some embodiments, the analysis server 1530 receives image data from a plurality of image data collection machines, aggregates the image data, processes the image data or the aggregated image data, and so on.

The rendering machine 1540 can include one or more processors 1544 coupled to a memory 1546 which can store and retrieve instructions and data, and it can also include a display 1542. The rendering of the resulting information rendering data 1554 can occur on the rendering machine 1540 or on a different platform from the rendering machine 1540. In embodiments, the rendering of the resulting information rendering data occurs on the image data collection machine 1520 or on the analysis server 1530. As shown in the system 1500, the rendering machine 1540 can receive resulting information rendering data 1554 via the Internet 1510 or another network from the image data collection machine 1520, from the analysis server 1530, or from both. The rendering can include a visual display or any other appropriate display format.

The system 1500 can include a computer program product embodied in a non-transitory computer readable medium for image analysis, the computer program product comprising code which causes one or more processors to perform operations of: obtaining an image of an individual; identifying a face of the individual; evaluating the individual to be within a sub-sectional component of a population; and performing an evaluation of content of the face based on the evaluating of the individual to be within the sub-sectional component of the population.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"— may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for image analysis comprising:
   obtaining an image of an individual;
   identifying a face of the individual utilizing a multilayered analysis engine comprising a neural network that includes an input layer;
   evaluating the individual to be within a sub-sectional component of a population; and
   performing, using one or more processors, an evaluation of content of the face based on the evaluating of the individual to be within the sub-sectional component of the population, wherein the performing the evaluation of content of the face is based on modulating a sensitivity to an emotional content by selecting a first threshold for the evaluation that is associated with the sub-sectional component of the population.

2. The method of claim 1 further comprising disambiguating among a plurality of content types for the content of the face based on the sub-sectional component of the population.

3. The method of claim 2 wherein the disambiguating is further based on experiential context for the individual.

4. The method of claim 1 wherein the sub-sectional component is determined based on a demographic.

5. The method of claim 4 wherein the demographic includes an age, ethnicity, culture, or gender.

6. The method of claim 4 wherein the evaluating the individual to be within the sub-sectional component is based on applying image classifiers to the face.

7. The method of claim 1 wherein the sub-sectional component is determined based on an activity in which the individual is participating.

8. The method of claim 1 wherein the sub-sectional component is determined based on information pertaining to prior experiential information for the individual.

9. The method of claim 1 wherein the performing the evaluation of the content of the face is based on modifying emotion classifiers.

10. The method of claim 9 wherein the modifying is based on the individual being within the sub-sectional component of the population.

11. The method of claim 1 wherein the performing the evaluation of the content of the face is based on a Bayesian framework.

12. The method of claim 11 wherein the Bayesian framework includes a conditional probability based on the individual being within the sub-sectional component of the population.

13. The method of claim 11 wherein the performing the evaluation of content of the face is further based on a prior probability that occurred.

14. The method of claim 1 wherein the identifying further comprises identifying a second face within the image.

15. The method of claim 14 further comprising:
   identifying a second face within the image;
   evaluating a person associated with the second face to be within a second sub-sectional component of the population; and
   performing an evaluation of content of the second face based on the evaluating of the person to be within a second sub-sectional component of the population.

16. The method of claim 15 wherein the sub-sectional component and the second sub-sectional component are identical.

17. The method of claim 14 wherein the face and the second face are from a plurality of people within the image.

18. The method of claim 1 wherein the evaluation of content of the face is based on a mental state event temporal signature.

19. The method of claim 1 further comprising:
   defining a region of interest (ROI) in the image that includes the face;
   extracting one or more histogram-of-oriented-gradients (HoG) features from the ROI; and
   computing a set of facial metrics based on the one or more HoG features.

20. The method of claim 1 further comprising:
   identifying multiple human faces within the image;
   defining a region of interest (ROI) in the image for each identified human face;
   extracting one or more histogram-of-oriented-gradients (HoG) features from each ROI; and
   computing a set of facial metrics based on the one or more HoG features for each of the multiple human faces.

21. A computer program product embodied in a non-transitory computer readable medium for image analysis, the computer program product comprising code which causes one or more processors to perform operations of:
obtaining an image of an individual;
identifying a face of the individual utilizing a multilayered analysis engine comprising a neural network that includes an input layer;
evaluating the individual to be within a sub-sectional component of a population; and
performing an evaluation of content of the face based on the evaluating of the individual to be within the sub-sectional component of the population, wherein the performing the evaluation of content of the face is based on modulating a sensitivity to an emotional content by selecting a first threshold for the evaluation that is associated with the sub-sectional component of the population.

22. A computer system for image analysis comprising:
a memory which stores instructions;
one or more processors attached to the memory wherein the one or more processors, when executing the instructions which are stored, are configured to:
obtain an image of an individual;
identify a face of the individual utilizing a multilayered analysis engine comprising a neural network that includes an input layer;
evaluate the individual to be within a sub-sectional component of a population; and
perform an evaluation of content of the face based on the evaluating of the individual to be within the sub-sectional component of the population, wherein the performing the evaluation of content of the face is based on modulating a sensitivity to an emotional content by selecting a first threshold for the evaluation that is associated with the sub-sectional component of the population.

23. The method of claim 1 wherein the modulating is based on the evaluating of the sub-sectional component.

24. The method of claim 15 wherein the performing the evaluation of content of the second face is based on modulating a sensitivity to an emotional content by selecting a second threshold for the evaluation that is associated with the second sub-sectional component of the population, wherein the first threshold and second threshold are different.

25. The method of claim 1 wherein the sub-sectional component of the population is an ethnicity.

26. The method of claim 1 wherein the modulating a sensitivity to an emotional content includes adjusting a gain of a sensitivity to the emotional content, wherein the gain is associated with the sub-sectional component of the population.

27. The method of claim 1 wherein the input layer performs edge detection on the image.

28. The method of claim 1 wherein performing the evaluation of content of the face further includes identifying a plurality of action units.

* * * * *